US012612654B2

(12) United States Patent
Wochner et al.

(10) Patent No.: US 12,612,654 B2
(45) Date of Patent: Apr. 28, 2026

(54) METHOD FOR ANALYZING RNA

(71) Applicant: CureVac SE, Tübingen (DE)

(72) Inventors: Aniela Wochner, Tübingen (DE);
Tilmann Roos, Kusterdingen (DE);
Fabian Johannes Eber, Tübingen
(DE); Philipp Hofmann, Stuttgart (DE)

(73) Assignee: CureVac SE, Tübingen (DE)

( * ) Notice: Subject to any disclaimer, the term of this
patent is extended or adjusted under 35
U.S.C. 154(b) by 559 days.

(21) Appl. No.: 16/077,366

(22) PCT Filed: Feb. 12, 2016

(86) PCT No.: PCT/EP2016/053047
§ 371 (c)(1),
(2) Date: Aug. 10, 2018

(87) PCT Pub. No.: WO2017/137095
PCT Pub. Date: Aug. 17, 2017

(65) Prior Publication Data
US 2021/0180106 A1     Jun. 17, 2021

(51) Int. Cl.
*C12Q 1/68*          (2018.01)
*C12Q 1/6806*        (2018.01)

(52) U.S. Cl.
CPC ...... *C12Q 1/6806* (2013.01); *C12Q 2531/113*
(2013.01); *C12Q 2565/518* (2013.01)

(58) Field of Classification Search
CPC ............ C12Q 1/6806; C12Q 2531/113; C12Q
2565/518
See application file for complete search history.

(56) References Cited

U.S. PATENT DOCUMENTS

| | | | |
|---|---|---|---|
| 7,074,596 B2 | 7/2006 | Darzynkiewicz et al. | |
| 2005/0032730 A1 | 2/2005 | Von der Mulbe et al. | |
| 2005/0059624 A1 | 3/2005 | Hoerr et al. | |
| 2005/0250723 A1 | 11/2005 | Hoerr et al. | |
| 2006/0188490 A1 | 8/2006 | Hoerr et al. | |
| 2006/0275747 A1* | 12/2006 | Hardy ................. | C12Q 1/6886 |
| | | | 435/5 |
| 2008/0025944 A1 | 1/2008 | Hoerr et al. | |
| 2008/0267873 A1 | 10/2008 | Hoerr et al. | |
| 2009/0324584 A1 | 12/2009 | Hoerr et al. | |

(Continued)

FOREIGN PATENT DOCUMENTS

| | | |
|---|---|---|
| EP | 1518928 | 3/2005 |
| EP | 2742951 | 6/2014 |

(Continued)

OTHER PUBLICATIONS

Wong et al., Real-time PCR for mRNA quantitation, Biotechniques.
Jul. 2005;39(1):75-85. doi: 10.2144/05391RV01.*

(Continued)

*Primary Examiner* — Aaron A Priest
(74) *Attorney, Agent, or Firm* — pH IP Law

(57)          ABSTRACT

The present invention relates to the field of RNA analysis. In
particular, the invention concerns the use of one or more
nucleic acid molecules for the analysis of an RNA molecule.
In particular, the method is suitable for use in quality control
during or following production of RNA. Furthermore, the
present invention provides methods for analyzing a mixture
of RNA molecules or an RNA population.

18 Claims, 5 Drawing Sheets

Specification includes a Sequence Listing.

A

B

(56) References Cited

U.S. PATENT DOCUMENTS

| | | | |
|---|---|---|---|
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2012/0021043 A1 | 1/2012 | Kramps et al. | |
| 2012/0258046 A1 | 10/2012 | Mutzke | |
| 2012/0258461 A1 | 10/2012 | Weisbart | |
| 2013/0129754 A1 | 5/2013 | Thess et al. | |
| 2013/0142818 A1 | 6/2013 | Baumhof et al. | |
| 2013/0259879 A1 | 10/2013 | Baumhof et al. | |
| 2013/0280283 A1 | 10/2013 | Lorenz et al. | |
| 2013/0295043 A1 | 11/2013 | Kallen et al. | |
| 2013/0336998 A1 | 12/2013 | Kallen et al. | |
| 2014/0322716 A1* | 10/2014 | Robins | C12Q 1/6881 |
| | | | 435/6.12 |
| 2015/0037326 A1 | 2/2015 | Butler-Ransohoff et al. | |
| 2015/0050302 A1 | 2/2015 | Thess | |
| 2015/0057340 A1 | 2/2015 | Thess et al. | |
| 2015/0093413 A1 | 4/2015 | Thess et al. | |
| 2015/0118183 A1 | 4/2015 | Baumhof | |
| 2015/0118264 A1 | 4/2015 | Baumhof et al. | |
| 2015/0165006 A1 | 6/2015 | Thess et al. | |
| 2015/0184195 A1 | 7/2015 | Thess et al. | |
| 2015/0218554 A1 | 8/2015 | Thess | |
| 2015/0306249 A1 | 10/2015 | Baumhof et al. | |
| 2015/0320847 A1 | 11/2015 | Thess et al. | |
| 2016/0024493 A1* | 1/2016 | Robins | C12Q 1/6846 |
| | | | 506/9 |
| 2016/0046949 A1 | 2/2016 | May et al. | |
| 2016/0130345 A1 | 5/2016 | Fotin-Mleczek et al. | |
| 2016/0166668 A1 | 6/2016 | Kallen et al. | |
| 2016/0166678 A1 | 6/2016 | Kallen et al. | |
| 2016/0166710 A1 | 6/2016 | Baumhof | |
| 2016/0166711 A1 | 6/2016 | Schnee et al. | |
| 2016/0168207 A1 | 6/2016 | Kramps et al. | |
| 2016/0168227 A1 | 6/2016 | Kallen et al. | |
| 2016/0235864 A1 | 8/2016 | Schlake et al. | |
| 2016/0304883 A1 | 10/2016 | Grund et al. | |
| 2016/0304938 A1 | 10/2016 | Wochner | |
| 2016/0326575 A1 | 11/2016 | Von Der Mulbe | |
| 2016/0331844 A1 | 11/2016 | Fotin-Mleczek et al. | |
| 2017/0014496 A1 | 1/2017 | Fotin-Mleczek et al. | |
| 2017/0029847 A1 | 2/2017 | Thess | |
| 2017/0114378 A1 | 4/2017 | Wochner et al. | |
| 2017/0183700 A1* | 6/2017 | Hamana | C12Q 1/68 |
| 2017/0202866 A1* | 7/2017 | Sampath | A61K 38/1709 |
| 2017/0252430 A1 | 9/2017 | Fotin-Mleczek et al. | |
| 2017/0326225 A1 | 11/2017 | Rauch et al. | |
| 2018/0044687 A1 | 2/2018 | Thess et al. | |
| 2018/0066325 A1* | 3/2018 | Kelleher | A61P 31/18 |
| 2018/0125952 A1 | 5/2018 | Fotin-Mleczek et al. | |
| 2018/0126003 A1 | 5/2018 | Hoerr | |
| 2018/0142275 A1 | 5/2018 | Roos et al. | |
| 2018/0147146 A1 | 5/2018 | Eber et al. | |
| 2018/0148727 A1 | 5/2018 | Grund et al. | |
| 2018/0201967 A1 | 7/2018 | Eber et al. | |
| 2018/0208957 A1 | 7/2018 | Roos et al. | |
| 2018/0214537 A1 | 8/2018 | Mutzke et al. | |
| 2018/0237786 A1 | 8/2018 | Schlake et al. | |
| 2018/0237817 A1 | 8/2018 | Roos et al. | |
| 2018/0243219 A1 | 8/2018 | Ketterer et al. | |
| 2018/0296663 A1 | 10/2018 | Hipp et al. | |
| 2018/0298372 A1 | 10/2018 | Funkner et al. | |
| 2018/0312545 A1 | 11/2018 | Baumhof et al. | |
| 2018/0371392 A1 | 12/2018 | Mayer et al. | |
| 2019/0010485 A1 | 1/2019 | Yazdan Panah et al. | |
| 2019/0017100 A1 | 1/2019 | Wochner et al. | |
| 2019/0024096 A1 | 1/2019 | Schmid et al. | |
| 2019/0040378 A1 | 2/2019 | Fotin-Mleczek et al. | |
| 2019/0049414 A1 | 2/2019 | Wochner et al. | |
| 2019/0083602 A1 | 3/2019 | Roos et al. | |
| 2019/0100784 A1 | 4/2019 | Eber et al. | |
| 2019/0125857 A1 | 5/2019 | Rauch et al. | |
| 2019/0133950 A1 | 5/2019 | Eber et al. | |
| 2019/0177714 A1 | 6/2019 | Kunze et al. | |
| 2019/0185859 A1 | 6/2019 | Fotin-Mleczek et al. | |
| 2019/0194760 A1 | 6/2019 | Koch et al. | |
| 2019/0225971 A1 | 7/2019 | Williams | |
| 2019/0241633 A1 | 8/2019 | Fotin-Mleczek et al. | |
| 2019/0249219 A1 | 8/2019 | Reichert et al. | |
| 2019/0336608 A1 | 11/2019 | Baumhof et al. | |
| 2019/0336611 A1 | 11/2019 | Baumhof et al. | |
| 2019/0343933 A1 | 11/2019 | Horscroft et al. | |
| 2019/0343942 A1 | 11/2019 | Fotin-Mleczek et al. | |
| 2019/0351044 A1 | 11/2019 | Jasny et al. | |
| 2019/0351047 A1 | 11/2019 | Jasny et al. | |
| 2019/0351048 A1 | 11/2019 | Rauch | |
| 2019/0381180 A1 | 12/2019 | Baumhof et al. | |
| 2020/0023076 A1 | 1/2020 | Fotin-Mleczek et al. | |
| 2020/0085852 A1 | 3/2020 | Fotin-Mleczek | |
| 2020/0085944 A1 | 3/2020 | Heidenreich et al. | |
| 2020/0149026 A1 | 5/2020 | Horscroft et al. | |
| 2020/0163878 A1 | 5/2020 | Baumhof et al. | |
| 2020/0179526 A1 | 6/2020 | Baumhof et al. | |
| 2020/0318097 A1 | 10/2020 | Funkner et al. | |
| 2020/0392572 A1 | 12/2020 | Yazdan Panah et al. | |
| 2021/0030864 A1 | 2/2021 | Petsch et al. | |
| 2021/0069315 A1 | 3/2021 | Baumhof et al. | |
| 2021/0162037 A1 | 6/2021 | Jasny et al. | |
| 2021/0170017 A1 | 6/2021 | Lutz et al. | |
| 2021/0180106 A1 | 6/2021 | Wochner et al. | |
| 2021/0205434 A1 | 7/2021 | Petsch et al. | |
| 2021/0260178 A1 | 8/2021 | Jasny et al. | |
| 2021/0261897 A1 | 8/2021 | Yazdan Panah et al. | |
| 2021/0361761 A1 | 11/2021 | Lutz et al. | |
| 2021/0379181 A1 | 12/2021 | Rauch et al. | |
| 2021/0403925 A1 | 12/2021 | Chevessier-Tünnesen et al. | |
| 2022/0040281 A1 | 2/2022 | Schwendt et al. | |
| 2022/0073962 A1 | 3/2022 | Schwenger et al. | |
| 2022/0133908 A1 | 5/2022 | Rejman et al. | |
| 2022/0144877 A1 | 5/2022 | Heinz et al. | |
| 2022/0211838 A1 | 7/2022 | Oostvogels et al. | |
| 2022/0233568 A1 | 7/2022 | Schlake et al. | |
| 2022/0296628 A1 | 9/2022 | Thess et al. | |
| 2022/0313813 A1 | 10/2022 | Rauch et al. | |
| 2022/0340641 A1 | 10/2022 | Aggarwal et al. | |
| 2023/0064106 A1 | 3/2023 | Heinz et al. | |

FOREIGN PATENT DOCUMENTS

| | | |
|---|---|---|
| WO | WO 2002/098443 | 12/2002 |
| WO | WO 2008/016473 | 2/2008 |
| WO | WO 2008/077592 | 7/2008 |
| WO | WO 2008/157688 | 12/2008 |
| WO | WO 2009/149253 | 12/2009 |
| WO | WO 2010/093820 | 8/2010 |
| WO | WO 2010/123501 | 10/2010 |
| WO | WO 2011/015347 | 2/2011 |
| WO | WO 2012/019630 | 2/2012 |
| WO | WO 2012/019780 | 2/2012 |
| WO | WO 2012/104360 | 8/2012 |
| WO | WO 2012/135805 | 10/2012 |
| WO | WO 2013/049231 | 4/2013 |
| WO | WO 2013/052523 | 4/2013 |
| WO | WO 2013/059475 | 4/2013 |
| WO | WO 2013/143700 | 10/2013 |
| WO | WO 2014/005038 | 1/2014 |
| WO | WO 2014/152659 | 9/2014 |
| WO | WO 2015/101416 | 7/2015 |
| WO | WO 2016/184576 | 11/2016 |
| WO | WO 2017/001058 | 1/2017 |
| WO | WO 2017/021546 | 2/2017 |
| WO | WO 2017/025447 | 2/2017 |
| WO | WO 2017/064146 | 4/2017 |
| WO | WO 2017/081110 | 5/2017 |
| WO | WO 2017/098468 | 6/2017 |
| WO | WO 2017/109134 | 6/2017 |
| WO | WO 2017/137095 | 8/2017 |
| WO | WO 2017/140345 | 8/2017 |
| WO | WO 2017/140905 | 8/2017 |
| WO | WO 2017/149139 | 9/2017 |

(56)         References Cited

FOREIGN PATENT DOCUMENTS

| WO | WO 2017/162297 | 9/2017 |
|----|----------------|--------|
| WO | WO 2017/182634 | 10/2017 |
| WO | WO 2017/186928 | 11/2017 |
| WO | WO 2017/191258 | 11/2017 |
| WO | WO 2017/191264 | 11/2017 |
| WO | WO 2017/191274 | 11/2017 |
| WO | WO 2017/203008 | 11/2017 |
| WO | WO 2017/212006 | 12/2017 |
| WO | WO 2017/212007 | 12/2017 |
| WO | WO 2017/212008 | 12/2017 |
| WO | WO 2017/212009 | 12/2017 |
| WO | WO 2018/078053 | 5/2018 |
| WO | WO 2018/096179 | 5/2018 |
| WO | WO 2018/104540 | 6/2018 |
| WO | WO 2018/167320 | 9/2018 |
| WO | WO 2018/172556 | 9/2018 |
| WO | WO 2018/211038 | 11/2018 |
| WO | WO 2019/008001 | 1/2019 |
| WO | WO 2021/123332 | 6/2021 |
| WO | WO 2021/254593 | 12/2021 |
| WO | WO 2022/023559 | 2/2022 |
| WO | WO 2022/043551 | 3/2022 |
| WO | WO 2022/049093 | 3/2022 |

OTHER PUBLICATIONS

Dougherty et al, Quantitative analysis of deadenylation-independent mRNA decay by a modified MBRACE assay, Methods Mol Biol. 2014;1125:353-71. doi: 10.1007/978-1-62703-971-0_28.*

Boyle et al, Evaluation of the impact of single nucleotide polymorphisms and primer mismatches on quantitative PCR, BMC Biotechnology 9 (2009): 75-75.*

Nakanishi et al, Hair roots as an mRNA source for mutation analysis of Usher syndrome-causing genes, J Hum Genet. Oct. 2010;55(10):701-3. doi: 10.1038/jhg.2010.83. Epub Jul. 1, 2010.*

Janeway et al, T-cell receptor gene rearrangement, in Immunobiology: The Immune System in Health and Disease. 5th edition, Janeway CA Jr, Travers P, Walport M, et al.; New York: Garland Science; 2001.*

Brunelle et al., "In vitro transcription from plasmid or PCR-amplified DNA", *Methods Enzymol.*, 530:101-114, 2013.

Desai and Shankar, "Single-strand-specific nucleases", *FEMS Microbiol. Rev.*, 26:457-491, 2003.

Geall et al., "RNA: the new revolution in nucleic acid vaccines", *Semin. Immunol.*, 25(2):152-159, 2013.

International Search Report and Written Opinion issued in corresponding PCT Application No. PCT/EP2016/053047, mailed on Aug. 9, 2016.

Kolpashchikov, "An elegant biosensor molecular beacon probe: challenges and recent solutions", *Scientifica*, 928783:1-17, 2012.

Li et al., "Ultrasensitive optical DNA biosensor based on surface immobilization of molecular beacon by a bridge structure", *Anal. Sci.*, 17: 1149-1153, 2001.

Maxwell et al., "Assay of DNA-RNA hybrids by S 1 nuclease digestion and adsorption to DEAE-cellulose filters", *Nucl. Acids. Res.*, 5(6):2033-2038, 1978.

Thompson and Sommercorn, "Use of a multiple S1 nuclease protection assay to monitor changes in RNA levels for type 1 phosphatase and several proto-oncogenes in response to insulin", *J. Biol. Chem.*, 267(9):5921-5926, 1992.

Vet and Marras, "Design and optimization of molecular beacon real-time polymerase chain reaction assays", In: *Oligonucleotide Synthesis*, Herdewijn, P. (ed.), 288:273-290, 2005.

Vet et al., "Multiplex detection of four pathogenic retroviruses using molecular beacons", *Proc. Natl. Acad. Sci. USA*, 96:6394-6399, 1999.

Zuker, "Mfold web server for nucleic acid folding and hybridization prediction", *Nucl. Acids Res.*, 31(13):3406-3415, 2003.

Heighway et al., "Coamplification in tumors of kras2, type 2 inositol 1,4,5 triphosphate receptor gene, and a novel human gene, krag", *Genomics*, 35(1):207-214, 1996.

Office Communication issued in corresponding European Pat. Appl. No. 16710101.3, mailed on Mar. 24, 2020.

Wong and Medrano, "Real-time PCR for mRNA quantitation", *Biotechniques*, 39(1):75-85, 2005.

Andrus et al., "Base Composition Analysis of Nucleosides Using HPLC", In: *Current Protocols in Nucleic Acid Chemistry*, John Wiley & Sons, Inc., p. 10.6.1-10.6.6, 2001.

Cohen et al., "High-performance capillary electrophoretic separation of bases, nucleosides, and oligonucleotides: retention manipulation via micellar solutions and metal additives", *Anal. Chem.*, 59(7):1021-1027, 1987.

Danneberg et al., "Sequence-specific RNA cleavage by PNA conjugates of the metal-free artificial ribonuclease tris(2-aminobenzimidazole)," *Beilstein Journal of Organic Chemistry*, 11:493-498, 2015.

Dogandzhiyski et al., "Studies on Tris(2-aminobenzimidazole)-PNA Based Artificial Nucleases: A Comparison of Two Analytical Techniques," *Bioconjugate Chemistry*, 26(12):2514-2519, 2015.

Eadie et al., "High-performance liquid chromatographic analysis of oligodeoxyribonucleotide base composition", *Anal. Biochem.*, 165(2):442-447, 1987.

Fotin-Mleczek et al., "Highly potent mRNA based cancer vaccines represent an attractive platform for combination therapies supporting an improved therapeutic effect", *J. Gene Med.*, 14(6):428-439, 2012.

Johnsen et al., "Hydrophilic interaction chromatography of nucleoside triphosphates with temperature as a separation parameter", *J. Chromatogr. A*, 1218(35):5981-5986, 2011.

Kamiya et al., "Mutagenic properties of oxidized GTP and ATP in in vitro transcription-reverse transcription", *Nucleic Acid Symposium Series*, 50:99-100, 2006.

Kammerer et al., "MALDI-TOF MS analysis of urinary nucleosides", *J. Am. Soc. Mass Spectrom.*, 16(6):940-947, 2005.

Kore et al., "Synthesis and biological validation of N7-(4-chlorophenoxyethyl) substituted dinucleotide cap analogs for mRNA translation", *Bioorg. Med. Chem.*, 21(15):4570-4574, 2013.

Kuzuya et al., "Selective activation of two sites in RNA by acridine-bearing oligonucleotides for clipping of designated RNA fragments," *Journal of the American Chemical Society*, 126(5):1430-1436, 2004.

Li et al., "Development of an isocratic HPLC method for catechin quantification and its application to formulation studies", *Fitoterapia*, 83:1267-1274, 2012.

Nees et al., "Detection of RNA Modifications by HPLC Analysis and Competitive ELISA", In: *Innate DNA and RNA Recognition*, Anders and Migliorni (eds), 1169:3-14, 2014.

Nunomura et al., "Oxidative damage to RNA in aging and neurodegenerative disorders", *Neurotox. Res.*, 22:231-248, 2012.

Office Communication issued in U.S. Appl. No. 16/081,863, mailed Feb. 24, 2023.

Shan et al., "Messenger RNA oxidation is an early event preceding cell death and causes reduced protein expression", *FASEB J.*, 21:2753-2764, 2007.

Shimelis et al., "Nuclease P1 digestion/high-performance liquid chromatography, a practical method for DNA quantitation", *J. Chromatog.*, 1117(2):132-136, 2006.

Stepinski et al., "Synthesis and properties of mRNAs containing the novel "anti-reverse" cap analogs 7-methyl(3'-O-methyl)GpppG and 7-methyl(3'-deoxy)GpppG", *RNA*, 7(10):1486-1495, 2001.

Su et al., "Quantitative analysis of ribonucleoside modifications in tRNA by HPLC-coupled mass spectrometry", *Nature Protoc.*, 9(4):828-841, 2014.

Tanaka et al., "RNA oxidation catalyzed by cytochrome c leads to its depurination and cross-linking, which may facilitate cytochrome c release from mitochondria", *Free Radic. Biol. Med.*, 53(4):854-862, 2012.

Theus and Liarakos, "A simple assay for determining the capping efficiencies of RNA polymerases used for in vitro transcription", *BioTechniques*, 9(5):610-615, 1990.

(56)                    References Cited

OTHER PUBLICATIONS

Wietstock, "DNA Composition Analysis by Nuclease Digestion and HPLC", *J. Chem. Ed.*, 72(10):950, 1995.

* cited by examiner

METHOD FOR ANALYZING RNA

This application is a national phase application under 35 U.S.C. § 371 of International Application No. PCT/EP2016/053047, filed Feb. 12, 2016, the entire contents of which are hereby incorporated by reference.

FIELD OF THE INVENTION

The present invention relates to the field of RNA analysis. In particular, the invention concerns the use of one or more nucleic acid molecules for the analysis of an RNA molecule. In particular, the method is suitable for use in quality control during or following production of RNA. Furthermore, the present invention provides methods for analyzing a mixture of RNA molecules or an RNA population.

BACKGROUND OF THE INVENTION

Ribonucleic acid (RNA) molecules represent an emerging class of drugs. RNA-based therapeutics may be used in immunotherapy, gene therapy and genetic vaccination, belonging to the most promising and quickly developing therapeutic fields of modern medicine. RNA-based therapeutics may provide highly specific and individual treatment options for the therapy of a large variety of diseases.

For certain medical treatments and applications it is desired to apply a mixture of RNA species. Examples of such RNA mixture based treatments may include the application of polyvalent RNA mixtures that provide protection against several serotypes of a pathogen (e.g., hemagglutinin (HA) from multiple serotypes of Influenza A and B virus); RNA mixtures that provide different antigens from one pathogen (e.g., different antigens from Influenza, such as HA, nucleoprotein (NP), neuraminidase (NA) etc.); RNA mixtures that provide protection against several isoforms or variants of a cancer antigen (e.g., prostate specific antigen (PSA) in the context of prostate carcinoma); RNA mixtures that provide different epitopes of an antigen; RNA mixtures that contain a cancer specific and/or patient specific mixture of cancer antigens (expressed antigens or mutated antigens); RNA mixtures that encode a variety of antibodies (e.g., antibodies that are targeted against different epitopes), or any other therapeutically active RNA mixture (e.g., encoding different isoforms of an enzyme for molecular therapy, different therapeutic proteins for treatment of an indication wherein several proteins have to be supplemented).

For the successful development of RNA based therapeutics, the production of RNA molecules as pharmaceutically active ingredients must be efficient in terms of yield, quality, safety and costs, especially when RNA is produced at a large scale. In the context of RNA mixture based treatments, it is required that different components (RNA species) of the drug product (RNA mixture) can be characterized, both in terms of identity, integrity and quantity (quality control). Such quality controls may be implemented during the RNA production and/or following RNA production and/or as a batch release quality control.

However, RNA mixture-based therapeutics can be composed of multiple RNA species of highly similar size and sequence (e.g., polyvalent vaccines composed of multiple similar antigens). Standard methods to discriminate RNA species of similar size such as agarose gel electrophoresis or analytic HPLC are not suitable.

Therefore, the characterization and quality control of RNA mixtures can be highly challenging, and should ideally be possible in one step.

Vet et al. (1999) Proc. Natl. Acad. Sci. USA 96: 6394-6399 describe a multiplex nucleic acid assay for the identification of four different pathogenic retroviruses by differently colored molecular beacons.

Thompson and Sommercorn (1992) J. Biol. Chem. 267 (9): 5921-5926 describe the analysis of changes in the cellular RNA in response to insulin by a multiple S nuclease assay.

An ideal method for the quality control of RNA mixtures should be fast, robust, and cost effective allowing for the characterization of any or all of the presence, quantity and integrity of all RNA species within a mixture of RNAs.

Hence, there is a need for methods for RNA analysis in particular in terms of cost-efficiency, robustness and the ability of the methods to discriminate highly similar RNA species in RNA mixtures.

SUMMARY OF THE INVENTION

Provided herein are methods for the analysis of RNA ("quality controls"), preferably for the analysis of RNA mixtures, by using single-stranded nucleic acid molecules binding to the RNA. The analysis includes the characterization of RNA identity, RNA integrity and RNA quantity. In particular, a molecular beacon assay, an S1-nuclease assay and an RT-qPCR method may be used in the methods of the present invention. These methods are particularly suitable for the analysis of RNA mixtures which may even comprise RNA species with similar length and/or sequence. They are also suitable for analyzing chemically modified RNA.

Said methods may be used in a target sequence independent manner by the detection of tags which have been introduced into the RNA sequence. The development of such methods is a major advantage in the art, and will improve the establishment of a robust and cost-effective quality control of (industrial) RNA mixture based therapeutics.

Accordingly, the present invention relates to a method for analyzing a sample comprising in vitro transcribed RNA, comprising determining the presence, integrity and/or quantity of at least one RNA species having a sequence comprising a target sequence in said sample using a nuclease protection assay or a molecular beacon assay.

The analysis may be independent of the target sequence of the at least one RNA species.

The target sequence may be a coding sequence.

In one embodiment the nuclease protection assay comprises the following steps:

a) contacting said sample with at least one single-stranded nucleic acid molecule comprising a nucleic acid sequence which is complementary to at least a part of the sequence of the at least one RNA species in said sample and a detectable label attached to said single-stranded nucleic acid molecule under conditions sufficient to form a double-stranded nucleic acid molecule between the at least one RNA species and the single-stranded nucleic acid molecule, thereby providing a sample comprising the double-stranded nucleic acid molecule;

b) contacting the sample comprising the double-stranded nucleic acid molecule with a nuclease specific for single-stranded nucleic acid molecules under conditions sufficient to degrade single-stranded nucleic acid molecules present in the sample; and c) detecting the double-stranded nucleic acid molecule by means of the detectable label.

The detectable label may be a fluorescent label.

In one embodiment the at least one single-stranded nucleic acid molecule further comprises a moiety enabling immobilization of the double-stranded nucleic acid molecule which moiety may be biotin.

The method may further comprise after step b) and before step c) a step b1) of immobilizing the double-stranded nucleic acid molecule to a solid surface.

The solid surface may be coated with streptavidin.

The RNA species may further comprise a sequence located 5' and/or 3' of the target sequence and the at least one single-stranded nucleic acid molecule may comprise a nucleic acid sequence which is complementary to said sequence located 5' and/or 3' of the target sequence of the at least one RNA species.

The target sequence may be a coding sequence and the at least one single-stranded nucleic acid molecule may comprise a nucleic acid sequence which is complementary to a sequence in an untranslated region of the at least one RNA species.

In one embodiment the sequence in an untranslated region of the at least one RNA species is a synthetic sequence.

The untranslated region may be the 5' or the 3' untranslated region of the at least one RNA species.

For determining the quantity of the at least one RNA species the method may additionally comprise a step c1) of generating a standard curve for the at least one single-stranded nucleic acid molecule and matching a signal obtained by detecting the double-stranded nucleic acid molecule with said standard curve.

For determining the integrity of the at least one RNA species step a) may comprise contacting said sample comprising in vitro transcribed RNA with at least two single-stranded nucleic acid molecules, each comprising a nucleic acid sequence which is complementary to a different part of the sequence of the at least one RNA species and a detectable label attached to each of said single-stranded nucleic acid molecules, under conditions sufficient to form a double-stranded nucleic acid molecule between the at least one RNA species and the at least two single-stranded nucleic acid molecules.

In one embodiment the at least one RNA species further comprises one sequence located 5' of the target sequence and another sequence located 3' of the target sequence and the sequence of a first single-stranded nucleic acid molecule may be complementary to said sequence located 5' of the target sequence of the at least one RNA species and the sequence of a second single-stranded nucleic acid molecule may be complementary to said sequence located 3' of the target sequence of the at least one RNA species.

The target sequence may be a coding sequence and the sequence of the first single-stranded nucleic acid molecule may be complementary to a sequence in the 5' untranslated region of the at least one RNA species and the sequence of a second single-stranded nucleic acid molecule may be complementary to a sequence in the 3' untranslated region of the at least one RNA species.

The method may additionally comprise a step c1) of generating a standard curve for each of the at least two single-stranded nucleic acid molecules and matching a signal obtained by detecting the double-stranded nucleic acid molecules with the standard curve for the corresponding single-stranded nucleic acid molecule.

In one embodiment the molecular beacon assay comprises the following steps:

a) contacting said sample comprising in vitro transcribed RNA with at least one molecular beacon having a single-stranded portion comprising a nucleic acid sequence which is complementary to at least a part of the sequence of the at least one RNA species under conditions sufficient to form a double-stranded nucleic acid molecule between the at least one RNA species and the single-stranded portion of the at least one molecular beacon;

b) detecting the double-stranded nucleic acid molecule by means of fluorescence emitted by the at least one molecular beacon.

The at least one RNA species may further comprise a sequence located 5' and/or 3' of the target sequence and the single-stranded portion of the at least one molecular beacon may comprise a nucleic acid sequence which is complementary to said sequence located 5' or 3' of the target sequence of the at least one RNA species.

The target sequence may be a coding sequence and the single-stranded portion of the at least one molecular beacon may comprise a nucleic acid sequence which is complementary to a sequence in an untranslated region of the at least one RNA species.

The sequence in an untranslated region of the at least one RNA species may be a synthetic sequence.

The untranslated region may be the 5' or the 3' untranslated region of the at least one RNA species.

For determining the quantity of the at least one RNA species the method may additionally comprise a step b1) of generating a standard curve for the at least one molecular beacon and matching a signal obtained by detecting the double-stranded nucleic acid molecule with said standard curve.

For determining the integrity of the at least one RNA species step a) may comprise contacting said sample comprising in vitro transcribed RNA with at least two molecular beacons, each comprising a single-stranded portion comprising a nucleic acid sequence which is complementary to a different part of the sequence of the at least one RNA species under conditions sufficient to form a double-stranded nucleic acid molecule between the at least one RNA species and the single-stranded portions of the at least two molecular beacons.

The at least one RNA species may further comprise one sequence located 5' of the target sequence and another sequence located 3' of the target sequence and the sequence of the single-stranded portion of a first molecular beacon may be complementary to said sequence located 5' of the target sequence of the at least one RNA species and the sequence of the single-stranded portion of a second molecular beacon may be complementary to said sequence located 3' of the target sequence of the at least one RNA species.

In one embodiment the target sequence is a coding sequence and the sequence of the single-stranded portion of the first molecular beacon is complementary to a sequence in the 5' untranslated region of the at least one RNA species and the sequence of the single-stranded portion of the second molecular beacon is complementary to a sequence in the 3' untranslated region of the at least one RNA species.

The method may additionally comprise a step b1) of generating a standard curve for each of the at least two molecular beacons and matching a signal obtained by detecting the double-stranded nucleic acid molecules with the standard curve for the corresponding molecular beacon.

The present invention also relates to a method for analyzing a sample comprising in vitro transcribed RNA, comprising determining the presence, integrity and/or quantity of at least one RNA species having a sequence comprising a target sequence in said sample using reverse transcription followed by quantitative PCR (RT-qPCR), wherein said analysis is independent of the target sequence of the at least one RNA species.

The target sequence may be a coding sequence.

In one embodiment the method comprises the following steps:

a) contacting said sample comprising in vitro transcribed RNA with at least one primer for reverse transcription under conditions sufficient for reverse transcription, thereby providing a sample containing cDNA corresponding to the at least one RNA species;

b) contacting the sample containing cDNA with at least one set of PCR primers under conditions sufficient for PCR amplification of the cDNA, wherein each PCR primer binds specifically to a part of the cDNA; and c) detecting the amplified DNA.

The RNA species may further comprise a sequence located 5' and/or 3' of the target sequence and wherein the at least one set of PCR primers may bind to said sequence located 5' and/or 3' of the target sequence.

In one embodiment the target sequence is a coding sequence and at least one set of PCR primers binds to a sequence in an untranslated region of the at least one RNA species.

The sequence in an untranslated region of the at least one RNA species may be a synthetic sequence.

The untranslated region may be the 5' and/or the 3' untranslated region of the at least one RNA species.

The amplified DNA may be detected and optionally quantified using a fluorescent dye.

In one embodiment the at least one RNA species further comprises one sequence located 5' of the target sequence and another sequence located 3' of the target sequence and wherein for determining the integrity of the at least one RNA species one set of PCR primers binds to said sequence located 5' of the target sequence and another set of PCR primers binds to said sequence located 3' of the target sequence.

The target sequence may be a coding sequence and for determining the integrity one set of PCR primers may bind to the 5' untranslated region and another set of PCR primers may bind to the 3' untranslated region.

The sample comprising in vitro transcribed RNA may comprise different RNA species which may have a similar size and/or a similar nucleic acid sequence.

In one embodiment the analysis comprises determining the presence, integrity and quantity of the at least one RNA species in said sample comprising in vitro transcribed RNA.

The present invention also relates to a method of analyzing a sample comprising different RNA species, each having a sequence comprising a target sequence and being prepared by RNA in vitro transcription, the method comprising determining the presence, integrity and/or quantity of each of the RNA species present in said sample using a nuclease protection assay, RT-qPCR or a molecular beacon assay.

The different RNA species in the sample may have similar length and/or similar sequence.

The analysis may be independent of the target sequence of the different RNA species.

The target sequence may be a coding sequence.

The nuclease protection assay may comprise the following steps:

a) contacting said sample comprising different RNA species with single-stranded nucleic acid molecules having different nucleic acid sequences, wherein each single-stranded nucleic acid molecule comprises:

a nucleic acid sequence which is complementary to at least a part of the sequence of one RNA species within the sample, but not to sequences of other RNA species within the sample; and a detectable label attached to said single-stranded nucleic acid molecule; under conditions sufficient to form a double-stranded nucleic acid molecule between the one RNA species within the sample and the corresponding single-stranded nucleic acid molecule;

b) contacting the sample comprising the double-stranded nucleic acid molecule with a nuclease specific for single-stranded nucleic acid molecules under conditions sufficient to degrade single-stranded nucleic acid molecules present in the sample; and c) detecting the double-stranded nucleic acid molecule by means of the detectable label.

The detectable label may be a fluorescent label and the single-stranded nucleic acid molecules having different sequences may comprise different detectable labels.

The single-stranded nucleic acid molecules may further comprise a moiety enabling immobilization of the double-stranded nucleic acid molecule.

The moiety enabling immobilization of the double-stranded nucleic acid molecule may be biotin.

In one embodiment the method may further comprise after step b) and before step c) a step b1) of immobilizing the double-stranded nucleic acid molecule to a solid surface.

The solid surface may be coated with streptavidin.

In one embodiment at least one RNA species further comprises a sequence located 5' and/or 3' of the target sequence and at least one single-stranded nucleic acid molecule comprises a nucleic acid sequence which is complementary to said sequence located 5' or 3' of the target sequence of said RNA species.

The target sequence may be a coding sequence and the at least one single-stranded nucleic acid molecule may comprise a nucleic acid sequence which is complementary to a sequence in an untranslated region of said RNA species.

The sequence in an untranslated region of the RNA species may be a synthetic sequence and the untranslated region may be the 5' and/or the 3' untranslated region of the RNA species.

For determining the quantity of each of the RNA species the method may additionally comprise a step c1) of generating a standard curve for each of the different single-stranded nucleic acid molecules and matching a signal obtained by detecting a double-stranded nucleic acid molecule with the standard curve for the corresponding single-stranded nucleic acid molecule.

For determining the integrity of each of the RNA species step a) may comprise contacting said sample with different sets of single-stranded nucleic acid molecules, wherein each set comprises at least two single-stranded nucleic acid molecules, each single-stranded nucleic acid molecule comprising a nucleic acid sequence which is complementary to a different part of the sequence of one RNA species, but which is not complementary to sequences of the other RNA species and a detectable label attached to said single-stranded nucleic acid molecule, under conditions sufficient to form a double-stranded nucleic acid molecule between at least one RNA species and at least one set of single-stranded nucleic acid molecules.

At least one RNA species may further comprise a sequence located 5' and/or 3' of the target sequence and the sequence of a first single-stranded nucleic acid molecule in a set may be complementary to a sequence located 5' of the target sequence of one RNA species and the sequence of a second single-stranded nucleic acid molecule in said set may be complementary to a sequence located 3' of the target sequence of said RNA species.

The target sequence may be a coding sequence and the sequence of the first single-stranded nucleic acid molecule may be complementary to a sequence in the 5' untranslated region of the coding sequence and the sequence of a second single-stranded nucleic acid molecule may be complementary to a sequence in the 3' untranslated region of the coding sequence.

The method may additionally comprise a step c1) of generating a standard curve for each of the at least two single-stranded nucleic acid molecules of each of the sets and matching a signal obtained by detecting the double-stranded nucleic acid molecules with the standard curve for the corresponding single-stranded nucleic acid molecule.

In one embodiment the molecular beacon assay comprises the following steps:
a) contacting said sample with different molecular beacons, wherein each molecular beacon has a single-stranded portion comprising a nucleic acid sequence which is complementary to at least part of the sequence of one RNA species within the sample, but not to sequences of other RNA species within the sample; under conditions sufficient to form a double-stranded nucleic acid molecule between the one RNA species and the single-stranded portion of the corresponding molecular beacon; and
b) detecting the double-stranded nucleic acid molecules by means of fluorescence emitted by each of the molecular beacons.

The different molecular beacons may comprise different fluorophore/quencher pairs.

At least one RNA species may further comprise a sequence located 5' and/or 3' of the target sequence and the single-stranded portion of at least one molecular beacon may comprise a nucleic acid sequence which is complementary to said sequence located 5' or 3' of the target sequence of said RNA species.

The target sequence may be a coding sequence and the single-stranded portion of the at least one molecular beacon may comprise a nucleic acid sequence which is complementary to a sequence in an untranslated region of said RNA species.

The sequence in an untranslated region of the RNA species may be a synthetic sequence and the untranslated region may be the 5' and/or the 3' untranslated region of the at least one RNA species.

For determining the quantity of each of the RNA species the method may additionally comprise a step c1) of generating a standard curve for each of the different molecular beacons and matching a signal obtained by detecting a double-stranded nucleic acid molecule with the standard curve for the corresponding molecular beacon.

For determining the integrity of each of the RNA species step a) may comprise contacting said sample with different sets of molecular beacons, wherein each set comprises at least two molecular beacons, each molecular beacon comprising a single-stranded portion which is complementary to a different part of the sequence of one RNA species, but which is not complementary to sequences of the other RNA species, under conditions sufficient to form a double-stranded nucleic acid molecule between at least one RNA species and at least one set of molecular beacons.

At least one RNA species may further comprise a sequence located 5' and/or 3' of the target sequence and the sequence of the single-stranded portion of a first molecular beacon in a set may be complementary to a sequence located 5' of the target sequence of one RNA species and the sequence of the single-stranded portion of a second molecular beacon in said set may be complementary to a sequence located 3' of the target sequence of said RNA species.

The target sequence may be a coding sequence and the sequence of the single-stranded portion of a first molecular beacon may be complementary to a sequence in the 5' untranslated region of the coding sequence and the sequence of the single-stranded portion of a second molecular beacon may be complementary to a sequence in the 3' untranslated region of the coding sequence.

The method may additionally comprise a step c1) of generating a standard curve for each of the at least two molecular beacons of each of the sets and matching a signal obtained by detecting the double-stranded nucleic acid molecules with the standard curve for the corresponding molecular beacon.

In one embodiment the RT-qPCR comprises the following steps:
a) contacting said sample with at least one primer for reverse transcription under conditions sufficient for reverse transcription, thereby providing a sample containing cDNA;
b) contacting the sample containing cDNA with different sets of PCR primers under conditions sufficient for PCR amplification of the cDNA, wherein each set of PCR primers is capable of binding to the cDNA corresponding to one RNA species within the sample, but not to the cDNA corresponding to other RNA species within the sample; and
c) detecting the amplified DNA.

At least one RNA species may further comprise a sequence located 5' and/or 3' of the target sequence and at least one set of PCR primers may bind to the cDNA corresponding to said sequence located 5' and/or 3' of the target sequence.

The target sequence may be a coding sequence and the at least one set of PCR primers may bind to the cDNA corresponding to a sequence in an untranslated region of the at least one RNA species.

The sequence in an untranslated region of the at least one RNA species may be a synthetic sequence and the untranslated region may be the 5' and/or the 3' untranslated region of the at least one RNA species.

The amplified DNA may be detected and optionally quantified using a fluorescent dye and a different fluorescent dye may be used for each amplified DNA corresponding to one RNA species.

At least one RNA species may further comprise a sequence located 5' and/or 3' of the target sequence and for determining the integrity of the at least one RNA species one set of PCR primers may bind to the cDNA corresponding to a sequence located 5' of the target sequence and another set of PCR primers may bind to the cDNA corresponding to a sequence located 3' of the target sequence.

The target sequence may be a coding sequence and for determining the integrity one set of PCR primers may bind to the cDNA corresponding to the 5' untranslated region and another set of PCR primers may bind to the cDNA corresponding to the 3' untranslated region of the at least one RNA species.

The present invention also relates to the use of any of the methods described herein for the quality control of RNA prepared by RNA in vitro transcription.

The present invention also relates to an expression vector comprising in 5' to 3' direction a promoter and operably linked thereto a nucleic acid sequence encoding a target sequence and at least one synthetic sequence located 5' and/or 3' of the target sequence.

The expression vector may comprise in 5' to 3' direction a promoter and operably linked thereto a nucleic acid sequence encoding a 5' untranslated region, a coding sequence and a 3' untranslated region, wherein the 5' and/or 3' untranslated region comprises a synthetic sequence.

The present invention also relates to an expression vector comprising in 5' to 3' direction a promoter and operably linked thereto a nucleic acid sequence encoding a 5' untranslated region, a multiple cloning site and a nucleic acid sequence encoding a 3' untranslated region, wherein the 5' and/or 3' untranslated region comprises a synthetic sequence.

The 3' untranslated region may comprise in 5' to 3' direction a poly(A) sequence or a polyadenylation sequence, a poly(C) sequence and a histone stem loop.

The 3' untranslated region may comprise the sequence according to SEQ ID No. 9.

The synthetic sequence may be located 3' of the poly(C) sequence and 5' of the histone stem-loop.

The synthetic sequence may be transcribed into an RNA having the sequence of any one of SEQ ID NOs. 18 to 21.

The present invention also relates to the use of any of the expression vectors described herein for the production of RNA by in vitro transcription.

The present invention also relates to a nucleic acid molecule consisting of the sequence according to any one of SEQ ID Nos. 5 to 8, wherein a fluorophore is attached to one end of the nucleic acid molecule and a quencher is attached to the other end of the nucleic acid molecule.

The fluorophore may be attached to the 5' end and the quencher may be attached to the 3' end of the nucleic acid molecule.

The present invention also relates to the use of a nucleic acid molecule as defined above in the analysis of RNA prepared by in vitro transcription.

(A) Four different plasmid vectors are shown that harbor four distinctive synthetic nucleic acid sequences in the 3' UTRs (black boxes 1-4). These nucleic acid sequences can be recognized and bound by molecular beacon probes, single-stranded 25 nucleic acid molecules used in the nuclease protection assay, or by specific primers in RT-qPCR. Any target sequence (e.g., insert type A, B, C, D) can be cloned into the vectors via multiple cloning sties (MCS).

(B) RNA products obtained from the plasmid vectors via RNA in vitro transcription. The four synthetic nucleic acid sequences in the 3' UTR allow for a reliable 30 detection of the RNA species via molecular beacons, nuclease protection assay or RT-qPCR, even in settings where the respective inserts have very similar sizes and sequences.

Figure 1:
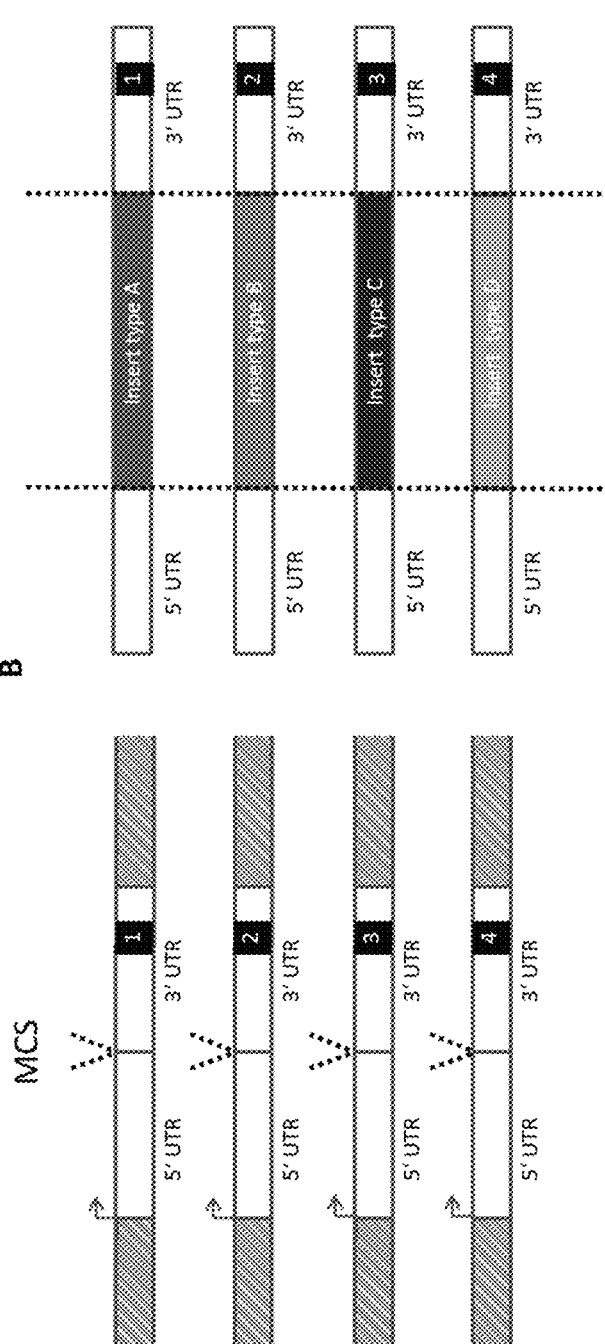
FIG. 1: Basic principle of mRNA analysis independent of the coding sequence of the RNA.
Figure 2:
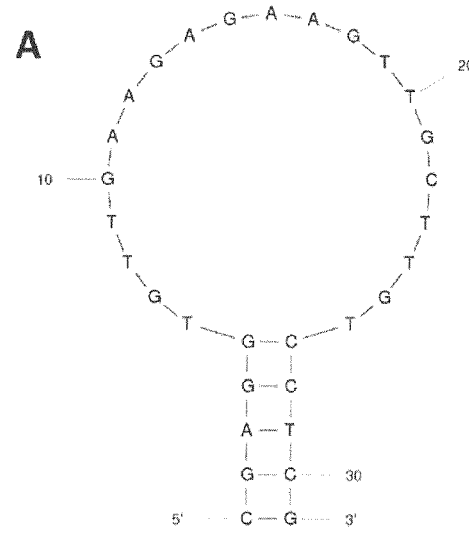
Figure 2:
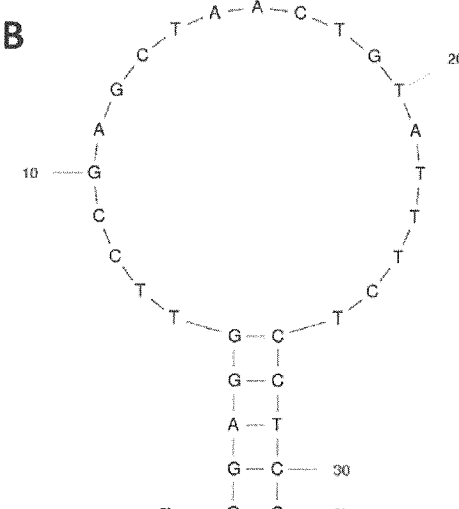
Figure 2:
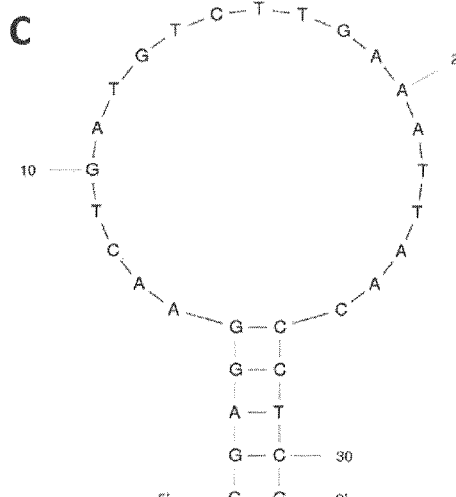
Figure 2:
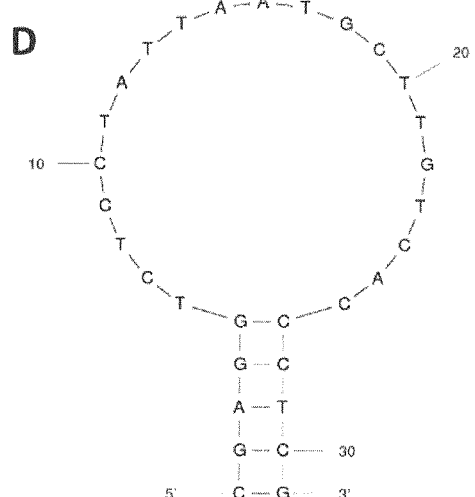

FIG. 2: Structure of the molecular beacons CU, FR, NU and SP as used herein generated according to best-design principles. The structure has been determined using mfold (Zuker (2003) Nucl. Acids Res. 31.13: 3406-3415.). (A) CU; (B) FR; (C) NU; (D) SP.

Figure 3:
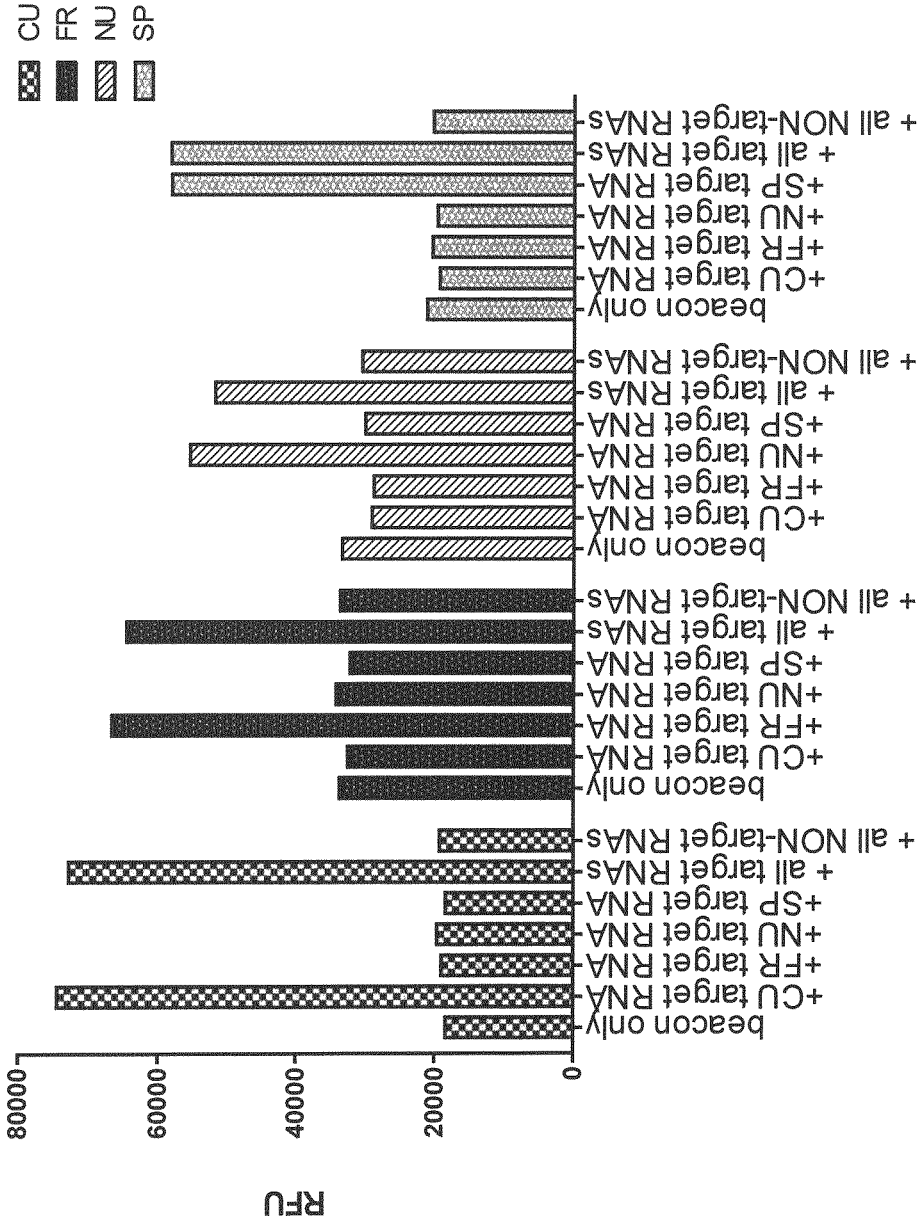

FIG. 3: Target binding and off target effects of the four molecular beacons CU, FR, NU and SP. RFU: relative fluorescence units.

Figure 4:
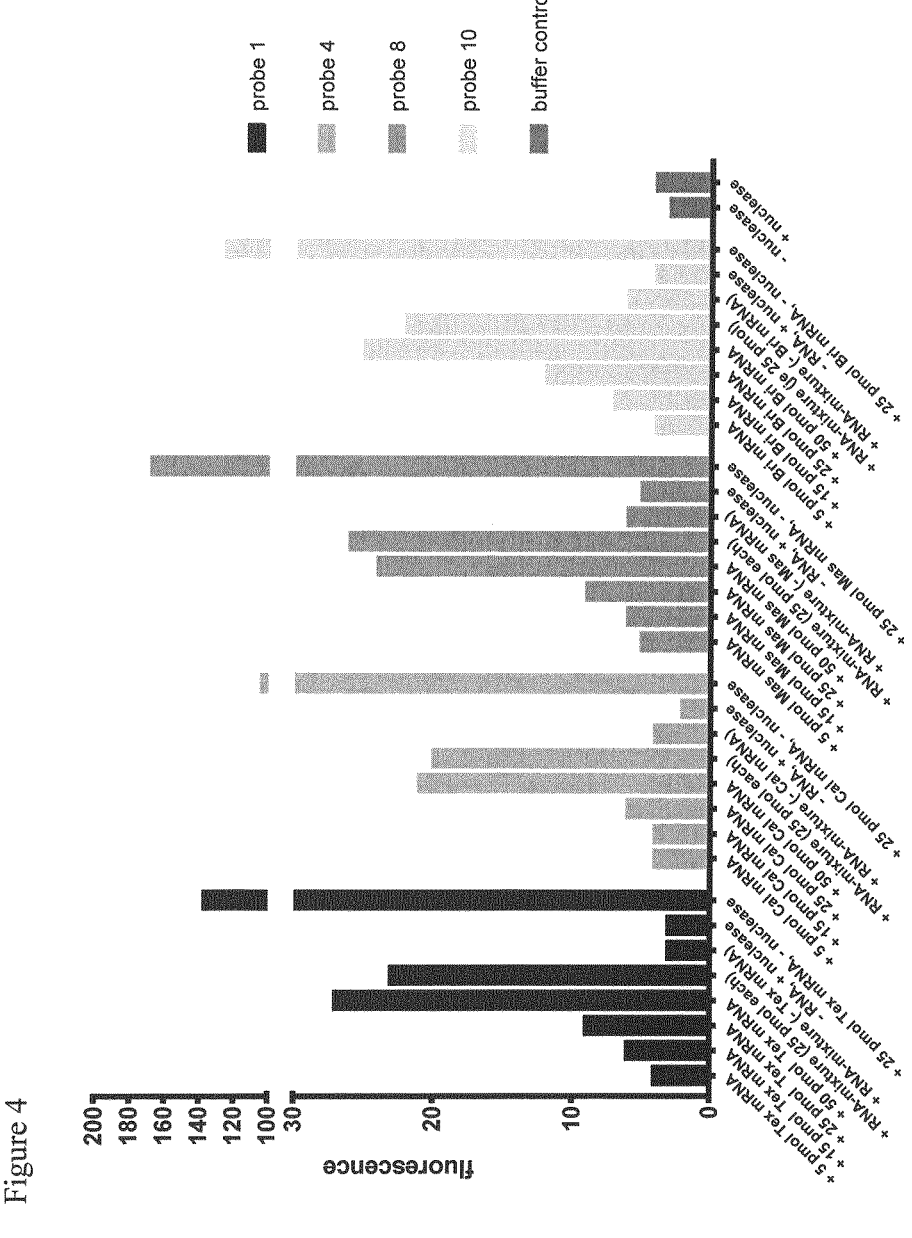

FIG. 4: Detection of target RNA in a concentration dependent manner using the respective DNA oligo probes in the inventive nuclease protection assay. The respective mRNA species and mRNA mixtures are indicated. Moreover, settings without RNA and without S1 nuclease treatment have been tested. In the figure, mRNA species are indicated as follows: "Tex"=H3N2 Influenza A virus (Texas/2012); "Cal"=H1N1 Influenza A virus (California/2009); "Mas"=HA Influenza B virus (Massachusetts/2012)); "Bri"=HA Influenza B virus (Brisbane/2008). For a detailed description of the experiment, see Example 7.

Figure 5:
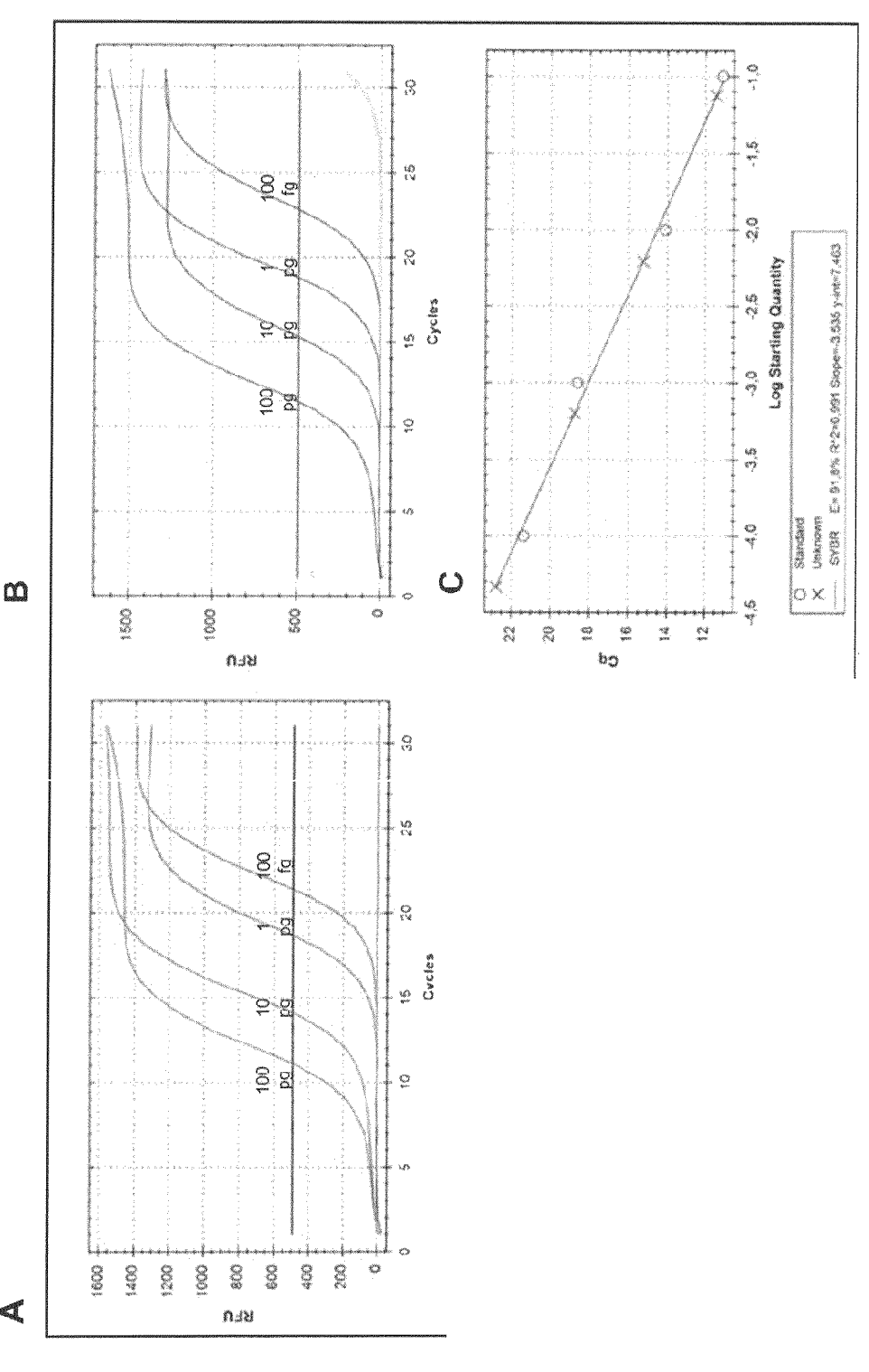

FIG. 5: Result of an exemplary two-step RT-qPCR (A) Two-step RT-qPCR with a primer pair for H3N2 Influenza A (Texas/2012) and H3N2 Influenza A (Texas/2012) as a template. These curves are used as standard curves.

(B) Two-step RT-qPCR with a primer pair for H3N2 Influenza A (Texas/2012) and a mixture of four different HA mRNAs.

(C) Experimentally determined standard curve which can be used for quantification. For a detailed description of the experiment, see Example 9.

DEFINITIONS

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art. Standard techniques are used for nucleic acid synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, NY), which are provided throughout this document.

RNA, mRNA: RNA is the usual abbreviation for ribonucleic acid. It is a nucleic acid molecule, i.e. a polymer consisting of nucleotide monomers. These nucleotides are usually adenosine-monophosphate (AMP), uridine-monophosphate (UMP), guanosine-monophosphate (GMP) and cytidine-monophosphate (CMP) monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, a coding sequence, optionally a 3'UTR and a poly(A) sequence.

In addition to messenger RNA, several non-coding types of RNA exist which may be involved in regulation of transcription and/or translation, and immunostimulation and which may also be produced by in vitro transcription. The term "RNA" further encompasses RNA molecules, such as viral RNA, retroviral RNA and replicon RNA, small inter-
fering RNA (siRNA), antisense RNA, CRISPR RNA,
ribozymes, aptamers, riboswitches, immunostimulating
RNA, transfer RNA (tRNA), ribosomal RNA (rRNA), small
nuclear RNA (snRNA), small nucleolar RNA (snoRNA),
microRNA (miRNA), and Piwi-interacting RNA (piRNA).

In vitro transcription: The term "in vitro transcription" or
"RNA in vitro transcription" relates to a process wherein
RNA is synthesized in a cell-free system (in vitro). DNA,
particularly plasmid DNA, is used as template for the
generation of RNA transcripts. RNA may be obtained by
DNA-dependent in vitro transcription of an appropriate
DNA template, which according to the present invention is
preferably a linearized plasmid DNA template. The pro-
moter for controlling in vitro transcription can be any
promoter for any DNA-dependent RNA polymerase. Par-
ticular examples of DNA-dependent RNA polymerases are
the T7, T3, and SP6 RNA polymerases. A DNA template for
RNA in vitro transcription may be obtained by cloning of a
nucleic acid, in particular cDNA corresponding to the
respective RNA to be in vitro transcribed, and introducing it
into an appropriate vector for in vitro transcription, for
example into plasmid DNA. In a preferred embodiment of
the present invention the DNA template is linearized with a
suitable restriction enzyme, before it is transcribed in vitro.
The cDNA may be obtained by reverse transcription of
mRNA or chemical synthesis. Moreover, the DNA template
for in vitro RNA synthesis may also be obtained by gene
synthesis.

Methods for in vitro transcription are known in the art
(Geall et al. (2013) Semin. Immunol. 25(2): 152-159;
Brunelle et al. (2013) Methods Enzymol. 530:101-14).

Reagents used in said method typically include:

1) a linearized DNA template with a promoter sequence
that has a high binding affinity for its respective RNA
polymerase such as bacteriophage-encoded RNA poly-
merases;
2) ribonucleoside triphosphates (NTPs) for the four bases
(adenine, cytosine, guanine and uracil);
3) optionally a cap analog as defined below (e.g. m7G
(5')ppp(5')G (m7G));
4) a DNA-dependent RNA polymerase capable of binding
to the promoter sequence within the linearized DNA
template (e.g. T7, T3 or SP6 RNA polymerase);
5) optionally a ribonuclease (RNase) inhibitor to inacti-
vate any contaminating RNase;
6) optionally a pyrophosphatase to degrade pyrophos-
phate, which may inhibit transcription;
7) MgCl$_2$, which supplies Mg$^{2+}$ ions as a co-factor for the
polymerase;
8) a buffer to maintain a suitable pH value, which can also
contain antioxidants (e.g. DT, and/or polyamines such
as spermidine at optimal concentrations.

In vitro transcribed RNA: An "in vitro transcribed RNA"
or "RNA prepared by in vitro transcription" is an RNA
molecule that has been synthesized from a template DNA,
commonly a linearized and purified plasmid (template)
DNA, a PCR product, or an oligonucleotide. Hence, the
composition of the sample comprising in vitro transcribed
RNA is determined by the template DNA which is subjected
to in vitro transcription. If only one template DNA is present
in the in vitro transcription reaction, the sample comprising
in vitro transcribed RNA will only comprise one RNA
species. If two or more different template DNAs are present
in the in vitro transcription reaction, the sample comprising
in vitro transcribed RNA will comprise two or more different
RNA species. The in vitro transcribed RNA is distinguished from the cellular RNA of an organism in that it comprises
only a limited number of different RNA species, which
number is determined by the number of the template DNA
in the in vitro transcription reaction.

RNA synthesis occurs in a cell free ("in vitro") assay
catalyzed by DNA dependent RNA polymerases. Particular
examples of DNA dependent RNA polymerases are the T7,
T3, and SP6 RNA polymerases. An in vitro transcribed
mRNA may comprise elements such as 5'-cap, optionally a
5'UTR, a coding sequence, optionally a 3'UTR and a poly
(A) sequence. Aside from proteinogenic messenger RNA,
several non-coding types of RNA exist which may be
involved in regulation of transcription and/or translation.
Such RNA molecules may also be synthesized by RNA in
vitro transcription.

Template DNA: As used herein, the term "template DNA"
(or "DNA template") typically relates to a DNA molecule
comprising a nucleic acid sequence encoding the RNA
sequence to be transcribed in vitro. The template DNA is
used as template for RNA in vitro transcription in order to
produce the RNA encoded by the template DNA. Therefore,
the template DNA comprises all elements necessary for
RNA in vitro transcription, particularly a promoter element
for binding of a DNA dependent RNA polymerase as e.g. T3,
T7 and SP6 RNA polymerases 5' of the DNA sequence
encoding the target RNA sequence. Furthermore the tem-
plate DNA may comprise primer binding sites 5' and/or 3' of
the DNA sequence encoding the target RNA sequence to
determine the identity of the DNA sequence encoding the
target RNA sequence e.g. by PCR or DNA sequencing. As
used herein, the term 'template DNA' may also refer to a
DNA vector, such as a plasmid DNA, which comprises a
nucleic acid sequence encoding the RNA sequence. Further,
the "template DNA" in the context of the present invention
may be a linear or a circular DNA molecule.

RNA species: The term "RNA species" denotes at least
one RNA of a group of the same RNA molecules which do
not differ in their RNA sequence and/or their sequence
length. Hence, the RNA molecules within one RNA species
are encoded by the same template DNA. If the RNA present
within the sample is a coding RNA, one RNA species
encodes one target peptide or protein.

different RNA species: The term "different RNA species"
denotes a number of RNA molecules which may differ with
respect to their RNA sequence and/or their sequence length.
If the RNA species are mRNA species, each of the different
RNA molecule species preferably encodes one target pep-
tide/protein. In the sample comprising different RNA species
which is analyzed by the method of the present invention,
identical, similar or different amounts of each species may
be present, preferably the amounts are identical or similar.
The number of different RNA molecule species which are
present in the composition can be 2, 3, 4, 5, 6, 7, 8, 9, 10,
11, 12, 13, 14, 15, 16, 17, 18, 19, 20, 21 and so forth. A
sample comprising different RNA species may be prepared
as described in PCT/EP2015/081000.

In the method of the present invention the different RNA
species may have a similar length, as the detection and
discrimination of the different RNA species is not dependent
on differences in the length. Hence, the length of the
different RNA species within the sample may differ by not
more than 10% or 8%, preferably not more than 7% or 6%,
more preferably by not more than 5% and most preferably
by not more than 4%.

In particular if the analysis is independent of the target
sequence of the different RNA species, the RNA species may
have a similar target sequence. For example, the target sequences of the different RNA species within the sample or a part of these target sequences may have a sequence identity of at least 70% or 75%, of at least 80% or 85%, or of at least 90%, 95% or even 100%. The sequence identity may be over a region comprising 200 nucleotides, 300 nucleotides, 400 nucleotides, 500 nucleotides or 600 nucleotides or over the complete target sequence.

Presence of an RNA species: This term is equivalent to the term "identity of an RNA species". In the analysis for presence or identity of an RNA species it is determined whether an RNA molecule with a specific nucleic acid sequence is present within the sample of RNA prepared by in vitro transcription to exclude those cases in which the RNA is not produced, although the corresponding template DNA was subjected to an RNA in vitro transcription reaction and those cases in which the RNA is produced, but has errors within its sequence so that its sequence does not 100% correspond to the sequence of the template DNA. Within the method of the present invention the presence of the RNA species may be determined by hybridizing at least one single-stranded nucleic acid molecule to a part of the RNA species and detecting any double strands formed.

Integrity of an RNA species: The term "integrity" describes whether the complete target RNA sequence is present in the sample of in vitro transcribed RNA. Low integrity could be due to, amongst others, degradation, cleavage, incorrect basepairing, integration of modified nucleotides or the modification of already integrated nucleotides, lack of or incomplete capping, lack of or incomplete polyadenylation, or incomplete transcription. Within the method of the present invention the integrity of the RNA species is determined by hybridizing at least two single-stranded nucleic acid molecules to different parts of the RNA species and detecting any double strands formed. Preferably one single-stranded nucleic acid molecule or set of primers binds to the 5' end of the RNA species and another single-stranded nucleic acid molecule or set of primers binds to the 3' end of said RNA species.

Quantity of an RNA species: The quantity of an RNA species in a sample is the number of copies of said RNA species present in said sample. Within the method of the present invention the quantity of the RNA species may either be determined directly in the reaction mixture (in case of RT-qPCR) or by comparison to a standard curve (in case of a nuclease protection assay or a molecular beacon assay).

Sequence of a nucleic acid molecule/nucleic acid sequence: The sequence of a nucleic acid molecule is typically understood to be the particular and individual order, i.e. the succession of its nucleotides. Within the present invention the sequence of an RNA species within the sample comprises a target sequence and may additionally comprise sequences located 5' and/or 3' of the target sequence.

Target sequence of an RNA species: The target sequence of an RNA species is the sequence or part of the sequence of the RNA species which is intended to provide a specific biological effect. Accordingly, the target sequence is selected such that it interacts with the cellular machinery in a specific, predetermined way. Examples of target sequences include the coding sequence of a peptide or protein or the sequence of viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

In constructs used for RNA in vitro transcription, i.e. constructs which provide the template DNA, the target sequence is the part of the construct which necessarily has to vary between different constructs, while all other components of the construct may remain the same, as they are not related to the biological function of the RNA. The target sequence does not comprise any additional sequences which are also transcribed in the RNA in vitro transcription reaction, but which do not provide or take part in the desired biological effect. In particular, it does not comprise any tag sequences or sequences which serve to enable or enhance the expression of the target sequence.

In particular embodiments, the target sequence is a coding sequence. In this case, the 5' and 3' untranslated regions flanking the coding sequence do not form part of the target sequence.

Coding sequence: The coding sequence is the RNA sequence which is translated into a peptide or protein. It therefore comprises a start codon, a number of nucleotides encoding the amino acids of the peptide or protein which is produced and a stop codon. Due to the three-letter code the total number of nucleotides within the coding sequence can be divided by three. The coding sequence may be flanked by 5' and 3' untranslated regions (UTRs). The coding sequence of a peptide or protein may be identical to the sequence within the organism from which it is derived or it may be optimized for translation efficiency and/or stability of the RNA, for example by optimizing the GC content of the coding sequence. Such optimized target sequences are described for example in WO 02/098443 A2.

5'-untranslated region (5'-UTR): A 5'-UTR is typically understood to be a particular section of messenger RNA (mRNA). It is located 5' of the coding sequence of the mRNA. Typically, the 5'-UTR starts with the transcriptional start site and ends one nucleotide before the start codon of the coding sequence. The 5'-UTR may comprise elements for controlling gene expression, also called regulatory elements. Such regulatory elements may be, for example, ribosomal binding sites. The 5'-UTR may be post-transcriptionally modified, for example by addition of a 5' cap structure. In the context of the present invention, the term "5'-UTR" typically refers to the sequence of an mRNA, which is located between the 5' cap structure and the start codon. Preferably, the 5'-UTR is the sequence, which extends from a nucleotide located 3' to the 5' cap structure, preferably from the nucleotide located immediately 3' to the 5' cap structure, to a nucleotide located 5' to the start codon of the coding sequence, preferably to the nucleotide located immediately 5' to the start codon of the coding sequence.

3'-untranslated region (3'-UTR): Generally, the term "3'-UTR" refers to a part of the RNA molecule, which is located 3' (i.e. "downstream") of a coding sequence and which is not translated into protein. Typically, a 3'-UTR is the part of an mRNA which is located between the protein coding region (coding sequence (CDS)) and the 3' terminus of the mRNA. In the context of the invention, the term 3'-UTR may also comprise elements, which are not encoded in the template, from which an RNA is transcribed, but which are added after transcription during maturation, e.g. a poly(A) sequence (or poly(A)'tail'). A 3'-UTR of the mRNA is not translated into an amino acid sequence. The 3'-UTR sequence is generally encoded by the DNA template, which is transcribed into the corresponding mRNA during the gene expression process. In the context of the present invention, a 3'-UTR corresponds to the sequence of a mature mRNA, which is located between the stop codon of the protein coding region, preferably immediately 3' to the stop codon of the protein coding region, and the poly(A) sequence of the mRNA.

Poly(A) sequence: A poly(A) sequence, also called poly (A) tail or 3'-poly(A) tail, is usually understood to be a sequence of adenine nucleotides, e.g., of up to about 400 adenosine nucleotides, e.g. from about 20 to about 400, preferably from about 50 to 20 about 400, more preferably from about 50 to about 300, even more preferably from about 50 to about 250, most preferably from about 60 to about 250 adenosine nucleotides, which is preferably added to the 3'-terminus of an mRNA. A poly(A) sequence is typically located at the 3'-end of an RNA, in particular mRNA. A poly(A) sequence may be located within an (m)RNA or any other nucleic acid molecule, such as, e.g., in a vector, for example, in a vector serving as template for the generation of an RNA, preferably an mRNA, e.g., by transcription of the vector. The term "poly(A) sequence" further comprises sequence elements, preferably artificial sequence elements, that are part of the 3'-UTR or located at the 3'-terminus of the artificial nucleic acid molecule, and which preferably comprise up to 1100 adenine nucleotides, more preferably at least 60, 70, 80, 90, 100, 110, 120, 130, 140, 150, 160, 170, 180, 190, 200, 210, 220, 230, 240, 250, 300, 350, 400, 500, 600, 700, 800, 900, or at least 1000 adenine nucleotides. In general, the poly(A) sequence consists of adenosine monophosphates.

Nuclease protection assay: A nuclease protection assay serves to detect and optionally characterize RNA molecules of known sequence in a sample which may comprise several different RNA species. It typically comprises a first step of contacting a sample comprising at least one RNA species with at least one single-stranded nucleic acid molecule comprising a nucleic acid sequence which is complementary to a sequence of the at least one RNA species and which further comprises a detectable label attached to the single-stranded nucleic acid molecule (also called "nucleic acid probe") under conditions to form a double-strand between the at least one RNA species and the corresponding single-stranded nucleic acid molecule. In a second step the sample comprising the double-stranded nucleic acid molecule formed by the RNA species and the single-stranded nucleic acid molecule is contacted with a nuclease which is specific for single-stranded nucleic acid molecules to degrade any single-stranded nucleic acid molecules which are present within the sample. Hence, only the double-stranded nucleic acid molecules formed between the RNA species and the single-stranded nucleic acid molecule remain within the sample. Finally, the double-stranded nucleic acid molecule formed by the RNA species and the single-stranded nucleic acid molecule is detected by means of the detectable label which is attached to the single-stranded nucleic acid molecule.

Nuclease specific for single-stranded nucleic acid molecules: A nuclease is an enzyme which interacts with nucleic acids and hydrolyzes the phosphodiester bonds between the nucleotides within a nucleic acid molecule. A nuclease which is specific for single-stranded nucleic acid molecules shows a high selectivity for single-stranded nucleic acid molecules and single-stranded regions within double-stranded nucleic acid molecules, but does not degrade double-stranded nucleic acid molecules such as double-stranded DNA, double-stranded RNA and DNA-RNA hybrids.

Suitable nucleases are described in Desai and Shankar (2003) FEMS Microbiology Reviews 26: 457-491 and include S1 nuclease from *Aspergillus oryzae*, mung bean nuclease, P1 nuclease from *Penicillium citrinum*, BAL31 nuclease from *Alteromonas espejiana, Neurospora crassa, Ustilago maydis*, exonuclease I, RecJ, exonuclease T, RNase ONE, ribonuclease A and ribonuclease T1. Within the method of the present invention preferably S1 nuclease is used.

Detectable label: A detectable label is a compound which is attached directly or indirectly to another molecule. Within the method of the present invention the detectable label is attached to a single-stranded nucleic acid molecule. The skilled person knows methods for attaching labels to nucleic acid molecules. Specific, non-limiting examples of labels include fluorescent and fluorogenic moieties, chromogenic moieties, haptens, affinity tags and radioactive isotopes. The label can be detectable directly (e.g. optically) or indirectly (e.g. by interaction with one or more molecules which are in turn detectable). Within the method of the present invention preferably fluorescent labels are used. The method of detecting the double-stranded nucleic acid molecules depends on the detectable label attached to the nucleic acid probe. For example, if the nucleic acid probe is labeled with a radioactive isotope, the double-stranded nucleic acid molecules are detected by autoradiography. If the nucleic acid probe is labeled with a fluorescent label, the double-stranded nucleic acid molecules are detected by fluorescence spectroscopy.

Complementary: Two nucleic acid sequences are complementary, if the bases forming a first nucleic acid sequence are able to form base pairs with the bases forming a second nucleic acid sequence by hydrogen bonds. Hydrogen bonds and therefore base pairs can be formed between a pyrimidine (i.e. cytosine, uracil, thymine and analogues thereof) and a purine (i.e. adenine, guanine and analogues thereof). In order to form a double strand two sequences do not need to be 100% complementary to each other. However, within the present invention the single-stranded nucleic acid molecules which serve as nucleic acid probes are preferably 100% complementary to the target sequence to enable a high level of quality control of the in vitro transcribed RNA.

Synthetic sequence: Within the present invention the term "synthetic sequence" is equivalent to the term "nucleic acid tag" and is intended to comprise a sequence which does not form part of the target sequence, but which is located 5' or 3' of the target sequence. The synthetic sequence is transcribed together with the target sequence in the process of RNA in vitro transcription and is therefore part of the same RNA molecule as the target sequence.

If the target sequence is a coding sequence, the synthetic sequence may be inserted into the 5' and/or 3' untranslated region. However, it is preferred that the insertion of the synthetic sequence does not destroy any functional elements within the untranslated regions. In particular, if it is inserted into the 5' untranslated region the synthetic sequence should not destroy the Kozak sequence (gccRccAUGG, with R being a purine) which is required for ribosome binding and initiation of translation. If it is inserted into the 3' untranslated region, it is preferably inserted between the elements of the 3' untranslated region, but not within these elements.

In particular embodiments, the 3' untranslated region used in the constructs for RNA in vitro transcription comprises a 3' UTR derived from a gene providing a stable mRNA, e.g. from an albumin gene, an α-globin gene, a β-globin gene, a tyrosine hydroxylase gene, a lipoxygenase gene, or a collagen alpha gene (particularly as disclosed in WO 2013/143700), a polyC region, a histone stem-loop structure (as disclosed in WO 2012/019780) and a polyA stretch. In this case, the synthetic sequence is preferably inserted between the polyC region and the histone stem-loop structure.

If the method used for RNA analysis is a nuclease protection assay or a molecular beacon assay, the length of the synthetic sequence is between 15 and 30 nucleotides. If the method used for RNA analysis is a reverse transcription/quantitative PCR assay, the length of the synthetic sequence is between 80 and 120 nucleotides.

The synthetic sequence is designed such that it can be specifically recognized by a single-stranded nucleic acid molecule, a single-stranded portion of a molecular beacon or a primer pair, meaning that the single-stranded nucleic acid molecule, single-stranded portion of a molecular beacon or primer pair forms a double strand with the synthetic sequence, but not with the target sequence. Therefore, the synthetic sequence has to be sufficiently distinct from the target sequence or parts thereof. Consequently, the design of the synthetic sequence is dependent on the target sequence. The synthetic sequence has a sequence identity of not more than 50% to the target sequence or a part thereof, preferably it has a sequence identity of not more than 45 or 40%, more preferably it has a sequence identity of not more than 35 or 30% and most preferably it has a sequence identity of not more than 25% or 20% to the target sequence or a part thereof. The part of the nucleic acid sequence comprises at least 15 or 20 nucleotides, preferably 25 or 30 nucleotides, more preferably 35 or 40 nucleotides and most preferably 45 or 50 nucleotides.

If a mixture of different RNA species is analyzed and more than one RNA species comprises a synthetic sequence, the synthetic sequences in the different RNA species have to be sufficiently distinct from each other to enable an accurate detection. Consequently, the design of the synthetic sequence is also dependent on other synthetic sequences present in the mixture of different RNA species. The synthetic sequences have a sequence identity of not more than 50% to each other, preferably they have a sequence identity of not more than 45 or 40% to each other, more preferably they have a sequence identity of not more than 35 or 30% and most preferably they have a sequence identity of not more than 25% or 20% to each other. The synthetic sequences are selected such that the synthetic sequences or the complementary sequences thereof are not able to form double strands under the conditions used in the nuclease protection assay, the molecular beacon assay or the RT-qPCR assay. The part of the nucleic acid sequence comprises at least 15 or 20 nucleotides, preferably 25 or 30 nucleotides, more preferably 35 or 40 nucleotides and most preferably 45 or 50 nucleotides.

Suitable synthetic sequences for the analysis of hemagglutinin coding sequences are described in the examples section.

Sequence identity Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences preferably relates to the percentage of nucleotides/amino acids of a sequence, which have the same position in two or more sequences having the same length.

Gaps are usually regarded as non-identical positions, irrespective of their actual position in an alignment.

The sequence identity may be determined using a series of programs, which are based on various algorithms, such as BLASTN, ScanProsite, the laser gene software, etc. As an alternative, the BLAST program package of the National Center for Biotechnology Information may be used with the default parameters. In addition, the program Sequencher (Gene Codes Corp., Ann Arbor, MI, USA) using the "dirtydata"-algorithm for sequence comparisons may be employed.

The identity between two protein or nucleic acid sequences is defined as the identity calculated with the program needle in the version available in April 2011. Needle is part of the freely available program package EMBOSS, which can be downloaded from the corresponding website. The standard parameters used are: gapopen 10.0 ("gap open penalty"), gapextend 0.5 ("gap extension penalty"), datafile EONAFULL (matrix) in the case of nucleic acids.

Standard curve: A standard curve is a type of graph used for determining quantities of an analyte. It is established by measuring multiple samples with known concentration (i.e. the standards) and plotting these concentrations against the measured values, such as radioactivity or fluorescence.

Molecular beacon assay: A molecular beacon is a nucleic acid molecule comprising a double-stranded stem formed by a first and a third nucleic acid sequence by basepairing and a single-stranded loop or portion formed by a second nucleic acid sequence. The single-stranded portion may hybridize to at least part of the sequence of the at least one RNA species in said sample. A fluorophore is attached to one of the nucleic acid sequences forming the stem and a quencher dye is attached to the other nucleic acid sequence forming the stem.

In the absence of a sequence which hybridizes to the single-stranded portion the fluorescence of the fluorophore is quenched by the quencher dye which is located closely to the fluorophore within the stem so that no fluorescence is emitted by the fluorophore. When the single-stranded portion binds to and forms a double strand with the sequence within the at least one RNA species, the double strand of the stem is disrupted, thereby separating the fluorophore from the quencher. Then the fluorescence emitted by the fluorophore can be detected by suitable means.

A review summarizing recent applications for molecular beacon technology is provided in Kolpashchikov (2012) *Scientifica*, Article ID 928783.

Typically, the stem of the molecular beacon is formed by nucleic acid sequences having a length of five to seven nucleotides, preferably of five nucleotides. The single-stranded portion or loop of the molecular beacon has a length of 15 to 30 nucleotides, preferably of 18 to 27 nucleotides and more preferably of 20 to 25 nucleotides. Since the specificity of the molecular beacon for a nucleic acid sequence is only determined by the single-stranded loop, molecular beacons with different specificities may comprise the same nucleotide sequences forming the stem and may only differ in the sequence of the single-stranded loop.

The design of molecular beacons is well-known to the expert and can be performed using methods and tools known in the art (e.g. "Design and optimization of molecular beacon real-time polymerase chain reaction assays." (In Herdewijn, P. (ed.)); Beacon Designer (Premier Biosoft International); Beacon Designer™ developed by PREMIER Biosoft International). The structure of the molecular beacons can be assessed using in silico structure predictions, e.g., using mfold web server.

Fluorophore: A fluorophore which is also called fluorochrome is a fluorescent chemical compound that can re-emit light upon light excitation. Fluorophores typically contain several combined aromatic groups, or plane or cyclic molecules with several π bonds. In the nuclease protection assay the fluorophore is covalently attached to the single-stranded nucleic acid molecule to provide a detectable label. In the molecular beacon assay the fluorophore is covalently attached to one of the nucleic acid sequences forming the double-stranded stem.

Fluorophores contemplated for use in the present invention include Alexa Fluor®350; Marina Blue®; Atto 390; Alexa Fluor® 405; Pacific Blue®; Atto 425; Alexa Fluor® 430; Atto 465; DY-485XL; DY-475XL; FAM™ 494; Alexa Fluor® 488; DY-495-05; Atto 495; Oregon Green® 488; DY-480XL 500; Atto 488; Alexa Fluor® 500; Rhodamin Green®; DY-505-05; DY-500XL; DY-510XL; Oregon Green® 514; Atto 520; Alexa Fluor® 514; JOE 520; TET™ 521; CAL Fluor® Gold 540; DY-521XL; Rhodamin 6G®; Yakima Yellow® 526; Atto 532; Alexa Fluor®532; HEX 535; VIC 538; CAL Fluor Orange 560; DY-530; TAMRA™; Quasar 570; Cy3™ 550; NED™; DY-550; Atto 550; Alexa Fluor® 555; DY-555; Alexa Fluor® 546; BMN™-3; DY-547; PET; Rhodamin Red®; Atto 565; CAL Fluor RED 590; ROX; Alexa Fluor® 568; Texas Red®; CAL Fluor Red 610; LC Red® 610; Alexa Fluor® 594; Atto 590; Atto 594; DY-600XL; DY-610; Alexa Fluor® 610; CAL Fluor Red 635; Atto 620; DY-615; LC Red 640; Atto 633; Alexa Fluor® 633; DY-630; DY-633; DY-631; LIZ 638; Atto 647N; BMN™-5; Quasar 670; DY-635; Cy5™; Alexa Fluor® 647; CEQ8000 D4; LC Red 670; DY-647 652; DY-651; Atto 655; Alexa Fluor® 660; DY-675; DY-676; Cy5.5™ 675; Alexa Fluor® 680; LC Red 705; BMN™-6; CEQ8000 D3; IRDye® 700Dx 689; DY-680; DY-681; DY-700; Alexa Fluor® 700; DY-701; DY-730; DY-731; DY-732; DY-750; Alexa Fluor® 750; CEQ8000 D2; DY-751; DY-780; DY-776; IRDye® 800CW; DY-782; and DY-781; Oyster® 556; Oyster® 645; IRDye® 700, IRDye® 800; WellRED D4; WellRED D3; WellRED D2 Dye; Rhodamine Red™; Rhodamine Red™; fluorescein; MAX 550 531 560 JOE NHS Ester (like Vic); TYE™ 563; TEX 615; TYE™ 665; TYE 705; ODIPY 493/503™; BODIPY 558/568™; BODIPY 564/570™; BODIPY 576/589™; BODIPY 581/591™; BODIPY TR-X™; BODIPY-530/550™; Carboxy-X-Rhodamine™; Carboxynaphthofluorescein; Carboxyrhodamine 6G™; Cascade Blue™; 7-Methoxycoumarin; 6-JOE; 7-Aminocoumarin-X; and 2', 4', 5', 7'-Tetrabromosulfonefluorescein.

Quencher: A quencher is a molecule which reduces the fluorescence intensity of a fluorophore by absorbing the excitation energy from the fluorophore. Suitable quenchers include, but are not limited to: Dabcyl; TAMRA; Black Hole Quenchers™; BHQ-16; BHQ-2®; BBQ-650; DDQ-1; Iowa Black RQ™; Iowa Black FQ™; QSY-21*; QSY-35®; QSY-7®; QSY-9®; QXL™ 490; QXL™ 570; QXL™ 610; QXL™ 670; QXL™ 680; DNP; and EDANS. Since individual fluorophores and quenchers are each optimally active at a particular wavelength or range of wavelengths, fluorophore and quencher pairs must be chosen such that the fluorophore's optimal excitation and emission spectra are matched to the quencher's effective range. This is particularly important in the case where several fluorophore-quencher pairs are used simultaneously. In such scenarios, suitable fluorophore-quencher combinations have to be used that do not interfere with each other (e.g., via fluorescence resonance energy transfer, FRET).

Reverse transcription: Reverse transcription is the process of generating complementary DNA (cDNA) from an RNA template. In this process an RNA template is incubated with the enzyme reverse transcriptase, deoxynucleotides and at least one suitable primer for a time and under conditions sufficient for cDNA synthesis to occur, e.g. incubation for thirty minutes to one hour at a temperature of 42° C. The primer(s) used for reverse transcription may be random so that any RNA present in a sample may be reverse transcribed into cDNA or may be target-specific so that only the target RNA is reverse transcribed into the corresponding cDNA.

Polymerase chain reaction (PCR): The polymerase chain reaction (PCR) is a technology in molecular biology used to amplify a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target sequence along with a heat-stable DNA polymerase, such as Taq polymerase, enable selective and repeated amplification. As PCR progresses, the DNA generated is itself used as a template for replication, setting in motion a chain reaction in which the DNA template is exponentially amplified. The DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the two DNA strands become templates for DNA polymerase to selectively amplify the target DNA. The selectivity of PCR results from the use of primers that are complementary to the DNA region targeted for amplification under specific thermal cycling conditions.

Quantitative Polymerase chain reaction (qPCR) or real-time polymerase chain reaction: A real-time polymerase chain reaction is a laboratory technique of molecular biology based on the polymerase chain reaction (PCR), which is used to amplify and simultaneously detect or quantify a targeted DNA molecule. The procedure follows the general principle of polymerase chain reaction (PCR); its key feature is that the amplified DNA is detected as the reaction progresses in "real time". Two common methods for the detection of products in quantitative PCR are: (1) non-specific fluorescent dyes that intercalate with any double-stranded DNA, such as SYBR® Green and (2) sequence-specific DNA probes consisting of oligonucleotides that are labelled with a fluorescent reporter, which permits detection only after hybridization of the probe with its complementary sequence to quantify nucleic acids.

Quantitative PCR is carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and DNA polymerase.

The PCR process generally consists of a series of temperature changes that are repeated 25-40 times. These cycles normally consist of three stages: the first, at around 95° C., allows the separation of the nucleic acid's double chain; the second, at a temperature of around 50-60° C., allows the binding of the primers with the DNA template; the third, at between 68-72° C., facilitates the polymerization carried out by the DNA polymerase. Due to the small size of the fragments the last step is usually omitted in this type of PCR as the enzyme is able to increase their number during the change between the alignment stage and the denaturing stage. In addition, some thermal cyclers add another short temperature phase lasting only a few seconds to each cycle, with a temperature of, for example, 80° C., in order to reduce the noise caused by the presence of primer dimers when a non-specific dye is used. The temperatures and the timings used for each cycle depend on a wide variety of parameters, such as: the enzyme used to synthesize the DNA, the concentration of divalent ions and deoxyribonucleotides (dNTPs) in the reaction and the bonding temperature of the primers. The type of quantitative PCR technique used depends on the DNA sequence in the samples, the technique can either use non-specific fluorochromes or hybridization probes.

RT-PCR: An RT-qPCR assay involves a first step of reverse transcription and a second step of quantitative PCR as described above. The reverse transcription reaction and the quantitative PCR reaction may be performed separately so that in a first reaction the RNA is reverse transcribed into cDNA and in a second reaction the cDNA is transferred into a new reaction mixture for the quantitative PCR. Alternatively, the reverse transcription reaction and the quantitative PCR reaction may be performed in one step so that the reaction mixture comprises both the components of the reverse transcription reaction and the components of the quantitative PCR.

Multiplex assay: A multiplex assay is an assay which measures multiple analytes in one single assay, i.e. simultaneously. In the context of the present invention it refers to methods which allow the detection of several RNA species within a mixture of RNA species in one sample and in one run. In case of the nuclease protection assay the multiplex analysis involves the use of a mixture of single-stranded nucleic acid molecules wherein each type of single-stranded nucleic acid differs from all other types of single-stranded nucleic acid molecules present within the mixture in both the nucleic acid sequence and the detectable label attached to it. In case of the molecular beacon assay the multiplex analysis involves the use of a mixture of molecular beacons wherein each type of molecular beacon differs from all other types of molecular beacons within the mixture in both the nucleic acid sequence of the single-stranded loop and the fluorophore attached to the stem. In case of the RT-qPCR assay the multiplex analysis involves the use of a mixture of primer pairs, wherein each type of primer pair differs from all other types of primer pairs present within the mixture in both the nucleic acid sequence and the detectable label attached to it.

Chemical modifications: The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Purification: as used herein, the term "purification" or "purifying" is understood to mean that the desired RNA in a sample is separated and/or isolated from impurities, intermediates, byproducts and/or reaction components present therein or that the impurities, intermediates, byproducts and/or reaction components are at least depleted from the sample comprising the RNA. Non-limiting examples of undesired constituents of RNA-containing samples which therefore need to be depleted may comprise degraded fragments or fragments which have arisen as a result of premature termination of transcription, or also excessively long transcripts if plasmids are not completely linearized. Furthermore, intermediates may be depleted from the sample such as e.g. template DNA. Additionally, reaction components such as enzymes, proteins, bacterial DNA and RNA, small molecules such as spermidine, buffer components etc. may have to be depleted from the RNA sample. In addition, impurities such as, organic solvents, and nucleotides or other small molecules may be separated. Preferably, the RNA is purified by a HPLC procedure as described in WO 2008/077592 A1. Ideally, the RNA has a higher purity and/or integrity after purification than the starting material. The purity may be determined by methods commonly known to the skilled person, e.g. by gas chromatography, quantitative PCR, analytical HPLC or gel electrophoresis.

Histone stem loop: A "histone stem-loop" or "histone 3' UTR stem loop" is derived from histone genes comprising an intramolecular base pairing of two neighbored entirely or partially reverse complementary sequences, thereby forming a stem-loop. The Histone 3' UTR stem-loop is an RNA element involved in nucleocytoplasmic transport of the histone mRNAs, and in the regulation of stability and of translation efficiency in the cytoplasm.

Such histone stem-loop elements have been introduced into the 3'UTRs of mRNAs to increase their translation efficiency, as described for example in WO 2012/019630 A1.

Poly(C) sequence: A poly(C) sequence, is understood to be a sequence of cytosine residues, e.g., of up to about 400 nucleotides, e.g. from about 20 to about 400, preferably from about 50 to about 400, more preferably from about 50 to about 300, even more preferably from about 50 to about 250, most preferably from about 60 to about 250 nucleotides, which is preferably added to the 3'-terminus of an RNA, in particular mRNA. A poly(C) sequence is typically located at the 3'-end of an (m)RNA.

DETAILED DESCRIPTION OF THE INVENTION

As discussed above, the present invention is based on the finding that in vitro transcribed RNA can be analyzed by molecular techniques using nucleic acid molecules which specifically hybridize to the RNA. The present invention may be practiced independent of the target sequence of the RNA and is therefore particularly suitable for the analysis of mixture of different RNA species, wherein the different RNA species within the mixture have similar sequence and/or similar length.

Accordingly, in one aspect the present invention relates to a method for analyzing a sample comprising in vitro transcribed RNA, comprising determining the presence, integrity and/or quantity of at least one RNA species having a sequence comprising a target sequence in said sample using a nuclease protection assay or a molecular beacon assay.

In one embodiment the analysis is independent of the target sequence of the at least one RNA species.

In another embodiment the sample may be analyzed by RT-qPCR independent of the target sequence of the at least one RNA species.

The analysis is independent of the target sequence, if the sequence of a nucleic acid molecule used for analyzing the RNA (single-stranded nucleic acid molecule in case of a nuclease protection assay, single-stranded portion or loop in case of a molecular beacon assay and primer pair in case of a RT-qPCR assay) is not complementary to a sequence within the target sequence and will therefore not form a double strand with the target sequence or a part of the target sequence. If the target sequence is a coding sequence, the sequence of a nucleic acid molecule used for analyzing the RNA is not complementary to the coding sequence or a part thereof.

The nuclease protection assay preferably comprises the following steps:

a) contacting said sample with at least one single-stranded nucleic acid molecule comprising a nucleic acid sequence which is complementary to at least a part of the sequence of the at least one RNA species in said sample and a detectable label attached to said single-stranded nucleic acid molecule under conditions sufficient to form a double-stranded nucleic acid molecule between the at least one RNA species and the single-stranded nucleic acid molecule, thereby providing a sample comprising the double-stranded nucleic acid molecule;

b) contacting the sample comprising the double-stranded nucleic acid molecule with a nuclease specific for single-stranded nucleic acid molecules under conditions sufficient to degrade single-stranded nucleic acid molecules present in the sample; and c) detecting the double-stranded nucleic acid molecule by means of the detectable label.

The single-stranded nucleic acid molecule which is complementary to at least a part of the RNA species and having a detectable label attached to it may also be called "nucleic acid probe". It may be an RNA or a DNA molecule, but preferably it is a DNA molecule.

The nucleic acid probe may be complementary to the target sequence or a part thereof, so that the analysis is dependent on the target sequence of the RNA species. Alternatively and preferably, the nucleic acid probe is complementary to a sequence of the RNA species which is not located within the target sequence, but 5' or 3' thereof. In this case, the analysis is independent of the target sequence of the RNA species.

The skilled person knows which conditions are sufficient to form a double-stranded nucleic acid molecule by the hybridization of two single-stranded nucleic acid molecules. Standard hybridization techniques are described for example in Sambrook et al., Molecular Cloning: A Laboratory Manual. 2nd edition, Cold Spring Harbor Laboratory, Cold Spring Harbor Laboratory Press, Cold Spring Harbor, N.Y., 1989. For example, the RNA species and the nucleic acid probe may be incubated in water containing 0.5 mM sodium EDTA. Alternatively, the hybridization solution may contain 0.2 M NaCl, 33 mM HEPES, pH 7.5 and 1 mM EDTA, pH 8.0. The hybridization may be performed by incubation of the mixture of single-stranded nucleic acid molecules at suitable temperatures such as 55° C.

The RNA species and the nucleic acid probe may be heated to 95° C., for example for 10 minutes, to resolve potential secondary structures before hybridization takes place. In case of complex secondary structures of the RNA species so called "openers" can be used to make the RNA more accessible for the nucleic acid probe. Openers are non-labelled nucleic acid sequences that bind to RNA regions other than the sequences to which the nucleic acid probe binds, and by creating double-stranded structures, open up the secondary structures of the target RNA. The use of such "openers" is preferred in embodiments where the analysis is dependent on the target sequence, and where binding of nucleic acid probes is hindered by secondary structures of the RNA.

To increase the likelihood of forming double strands between the RNA species and the nucleic acid probe the amount of the nucleic acid probe within the hybridization mixture may be higher than the amount of the RNA species. For example, the ratio of the nucleic acid probe to the RNA species may be in the range of 2:1 to 10:1, preferably 3:1 to 7:1 and more preferably it may be 4:1.

The skilled person is aware of conditions sufficient to degrade single-stranded nucleic acid molecules by a nuclease specific for single-stranded nucleic acid molecules. Some of the nucleases which are specific for single-stranded nucleic acid molecules such as the S1 nuclease or the mung bean nuclease are commercially available and supplied with buffers optimized to support their action. A suitable buffer contains NaCl, sodium acetate and zinc sulfate in suitable amounts.

The sample containing the double-stranded nucleic acid molecule is incubated with the nuclease specific for single-stranded nucleic acid molecules at a suitable temperature and for sufficient time to obtain complete degradation of single-stranded nucleic acid molecules. Such suitable conditions comprise a temperature of 25° C. and an incubation time of 15 minutes or a temperature of 37° C. and an incubation time of one hour.

After the incubation the nuclease may be inactivated by treatment with a proteinase or by incubation with ammonium acetate, EDTA and tRNA.

To remove the low-molecular weight products of the nuclease treatment before detecting the double-stranded nucleic acid molecule the double-stranded nucleic acid molecule may be precipitated and the precipitate may be collected on filters.

Alternatively, the double-stranded nucleic acid molecules may be bound to DEAE filters and the low molecular weight products may be removed by washing before the double-stranded nucleic acid molecule is analyzed by means of the detectable label (see Maxwell et al. (1978) Nucl. Acids. Res. 5(6): 2033-2038).

In another embodiment the double-stranded nucleic acid molecule may be immobilized by specific interaction of the double-stranded nucleic acid molecule with the solid substrate. Hence, the nucleic acid probe may further comprise a moiety enabling immobilization of the double-stranded nucleic acid molecule. In one embodiment, the moiety enabling immobilization may comprise a protein or peptide which has a specific affinity to another molecule which is itself coupled to the solid substrate. Such moieties include the biotin protein which has specific affinity to streptavidin, the polyhistidine tag which has specific affinity to metal ions and glutathione S transferase which has specific affinity to glutathione. Another moiety enabling immobilization is a moiety which enables covalent immobilization such as a thiol or sulfhydryl moiety which can be immobilized on sulfhydryl-binding plates.

In a particular embodiment the nucleic acid probe comprises a fluorescent label coupled to one end of the nucleic acid probe and a biotin moiety coupled to the other end of the nucleic acid probe. In an even more preferred embodiment, the fluorescent label such as Cy3 is attached to the 5' end of the nucleic acid probe and the biotin moiety is attached to the 3' end of the nucleic acid probe.

In one embodiment the double-stranded nucleic acid molecule is immobilized to a solid surface after treatment with the nuclease specific for single-stranded nucleic acid molecules and before detecting the double-stranded nucleic acid molecule. Preferably, the double-stranded nucleic acid molecule is immobilized by interaction of the moiety enabling immobilization with the solid surface, more preferably the double-stranded nucleic acid molecule is immobilized by interaction of biotin with streptavidin which is coated on the solid surface.

The solid surface may comprise metals, silicon, glass, polydimethylsiloxane (PDMS), plastic materials, porous membranes, papers, alkoxysilane-based sol gels, agarose, sepharose, polymethylacrylate, polyacrylamide, cellulose, and silica, monolithic supports, and expanded-bed adsorbents.

After immobilization the solid surface is preferably washed one or more times before the double-stranded nucleic acid molecule is detected via the detectable label. Suitable washing conditions are known to the skilled person and are selected such that they do not disrupt the binding between the RNA species and the nucleic acid probe. For example, the solid surface may be washed with TBS-T (tris buffered saline with Tween 20) for two to four times to remove any unbound molecules and products of the nuclease treatment.

As discussed above, the method of detecting the double-stranded nucleic acid molecule depends on the detectable label attached to the single-stranded nucleic acid molecule or nucleic acid probe. If the detectable label is a fluorescent label, the double-stranded nucleic acid molecules are detected by fluorescence spectroscopy. If the nucleic acid probe is labeled with a radioactive isotope, the double-stranded nucleic acid molecules are detected by autoradiography.

For determining the quantity of the at least one RNA species in a nuclease protection assay, the signal of the detectable label obtained with known concentrations of the nucleic acid probe is plotted against the concentration to establish a curve. If then the signal obtained with the double-stranded nucleic acid molecule formed by the RNA species and the nucleic acid probe is measured, it can be matched with the corresponding datapoint on the standard curve, thereby providing the information on the concentration of the RNA species which is equimolar with that of the nucleic acid probe which is detected.

The nuclease protection assay may also be used to determine the integrity of the RNA species by contacting the RNA species with at least two different nucleic acid probes, wherein each of the at least two nucleic acid probes is complementary to a different part of the sequence of the at least one RNA species. Hence, a first double-stranded nucleic acid molecule is formed between the first nucleic acid probe and a first part of the sequence of the at one RNA species and a second double-stranded nucleic acid molecule is formed between the second nucleic acid probe and a second part of the sequence of the at one RNA species. The amount of each of the double-stranded RNA molecules can be determined as described above by using a standard curve for each of the nucleic acid probes. If the amount of the first double-stranded nucleic acid molecule is substantially the same as the amount of the second double-stranded nucleic acid molecule, the RNA species is considered to have integrity.

Preferably, the first and second nucleic acid probe bind to opposite ends of the RNA species, such as the 5' end of the RNA species and the 3' end of the RNA species. If the analysis is independent of the target sequence, the first and second nucleic acid probe preferably bind to sequences located 5' of the target sequence and 3' of the target sequence, such as a sequence in the 5' untranslated and the 3' untranslated region, if the target sequence is a coding sequence.

The contacting of the RNA species with the at least two different nucleic acid probes can take place in parallel reactions, so that one part of the sample comprising RNA prepared by in vitro transcription is contacted with the first nucleic acid probe and another part of said sample is contacted with the second nucleic acid probe in a separate reaction. In this case, the detectable label attached to the first and the second nucleic acid probe can be the same or different.

Alternatively, the integrity of the RNA species can be analyzed in a multiplexed reaction so that the sample comprising RNA prepared by in vitro transcription is contacted with the first and the second nucleic acid probe in one reaction. In this case, the detectable label attached to the first and the second nucleic acid probe has to be different so that the double-stranded nucleic acid molecules formed can be distinguished from each other. If the detectable labels in the multiplexed reaction are fluorescent labels, they have to be selected so that they do not interfere with each other, i.e. that the spectrum of light emitted by the fluorescent labels does not overlap.

The nuclease protection assay may also be used to analyze a sample comprising a mixture of different RNA species which have been prepared by RNA in vitro transcription. For this analysis said sample is contacted with different nucleic acid probes, wherein each nucleic acid probe has a sequence which is complementary to at least part of the sequence of one RNA species within the sample, but not to sequences of other RNA species within the sample. The nucleic acid probe which has a sequence which is complementary to at least part of the sequence of one RNA species within the sample, but not to sequences of other RNA species within the sample is also called "corresponding nucleic acid probe" wherein the correspondence relates to the RNA species for which the nucleic acid probe is specific.

For each of the RNA species present within said sample at least one nucleic acid probe is used. Hence, if a sample comprises n different RNA species, the analysis is performed with at least n different nucleic acid probes. If the analysis involves determining the presence and/or the quantity of each of the RNA species within the sample, the analysis is performed with n different nucleic acid probes. If the analysis involves determining the integrity of each of the RNA species within the sample, the analysis is performed with y×n nucleic acid probes, wherein y is the number of nucleic acid probes for one RNA species and is preferably 2.

The contacting of the different RNA species with the corresponding nucleic acid probes can take place in parallel reactions, so that one part of the sample comprising the mixture of RNA species is contacted with a nucleic acid probe corresponding to a first RNA species and another part of said sample is contacted with a nucleic acid probe corresponding to a second RNA species in a separate reaction. In this case, the detectable label attached to the first and the second nucleic acid probe can be the same or different.

Alternatively, the different RNA species can be analyzed in a multiplexed reaction so that the sample comprising the mixture of RNA species is contacted with the nucleic acid probes corresponding to each of the RNA species in one reaction. In this case, the detectable label attached to the different nucleic acid probes has to be different so that the double-stranded nucleic acid molecules formed can be distinguished from each other. If the detectable labels in the multiplexed reaction are fluorescent labels, they have to be selected so that they do not interfere with each other, i.e. that the spectrum of light emitted by the fluorescent labels does not overlap.

As discussed above, the analysis of the RNA species may be independent of the target sequence of these species. In this case, each of the RNA species preferably comprises a synthetic sequence or tag which is located 5' or 3' of the target sequence of the RNA species. The synthetic sequence has to be selected such that the nucleic acid probe which is intended to detect the corresponding RNA species within the sample binds only to the synthetic sequence of that RNA species, but not to the synthetic sequence of other RNA species within the mixture. Hence, the synthetic sequences have to be sufficiently different from each other to avoid the binding of the nucleic acid probes to multiple synthetic sequences. For the same reason, the synthetic sequences also have to be sufficiently different from the target sequence of each of the RNA species within the mixture.

In other embodiments the nucleic acid probe may be directed to an element which is naturally present within the 5' or 3' UTR of the RNA species and has not been inserted for detection purposes, but to have an effect on the transcribed RNA molecule. In this case, the different RNA species have to comprise different 5' or 3' UTRs to enable the detection.

In another embodiment a molecular beacon assay may be used to analyze a sample comprising in vitro transcribed RNA.

The molecular beacon assay may comprise the following steps:
a) contacting said sample with at least one molecular beacon having a single-stranded portion (also single-stranded loop) comprising a nucleic acid sequence which is complementary to at least a part of the sequence of the at least one RNA species under conditions sufficient to form a double-stranded nucleic acid molecule between the at least one RNA species and the single-stranded portion of the at least one molecular beacon;
b) detecting the double-stranded nucleic acid molecule by means of fluorescence emitted by the at least one molecular beacon.

The single-stranded loop of the molecular beacon may be complementary to the target sequence or a part thereof, so that the analysis is dependent on the target sequence of the RNA species. Alternatively and preferably, the single-stranded loop of the molecular beacon is complementary to a sequence of the RNA species which is not located within the target sequence, but 5' or 3' thereof. In this case, the analysis is independent of the target sequence of the RNA species.

The skilled person knows which conditions are sufficient to form a double-stranded nucleic acid molecule between an RNA molecule and a molecular beacon. For example, the RNA species and the molecular beacon may be incubated in 100 mM Tris/HCl and 100 mM NaCl at a temperature of 95° C. for five minutes, before the mixture is cooled to 25° C. and incubated at this temperature for 40 minutes. To increase the likelihood of forming double strands between the RNA species and the single-stranded portion of the molecular beacon the amount of the molecular beacon within the hybridization mixture may be higher than the amount of the RNA species. For example, the ratio of the molecular beacon to the RNA species may be in the range of 2:1 to 10:1, preferably 3:1 to 7:1 and more preferably it may be 4:1. After incubation the mixture may be directly analyzed in a fluorescence reader.

The double-stranded nucleic acid molecule formed by the RNA species and the single-stranded loop of the molecular beacon may be immobilized by specific interaction of the double-stranded nucleic acid molecule with the solid substrate. Hence, the molecular beacon may further comprise a moiety enabling immobilization of the double-stranded nucleic acid molecule. In one embodiment, the moiety enabling immobilization may comprise a protein or peptide which has a specific affinity to another molecule which is itself coupled to the solid substrate. Such moieties include the biotin protein which has specific affinity to streptavidin, the polyhistidine tag which has specific affinity to metal ions and glutathione S transferase which has specific affinity to glutathione. Another moiety enabling immobilization is a moiety which enables covalent immobilization such as a thiol or sulfhydryl moiety which can be immobilized on sulfhydryl-binding plates.

The moiety enabling immobilization, for example biotin, may be attached to the stem portion of the molecular beacon. An example for a biotinylated molecular beacon is provided in Li et al. (2001) Anal. Sci. 17: 1149-1153.

Preferably, the molecular beacon is immobilized to a solid surface before it is contacted with the sample comprising in vitro transcribed RNA. Preferably, the double-stranded nucleic acid molecule is immobilized by interaction of the moiety enabling immobilization with the solid surface, more preferably the double-stranded nucleic acid molecule is immobilized by interaction of biotin with streptavidin which is coated on the solid surface.

The solid surface may comprise metals, silicon, glass, polydimethylsiloxane (PDMS), plastic materials, porous membranes, papers, alkoxysilane-based sol gels, agarose, sepharose, polymethylacrylate, polyacrylamide, cellulose, and silica, monolithic supports, and expanded-bed adsorbents.

For determining the quantity of the at least one RNA species in a molecular beacon assay, the fluorescence obtained with known concentrations of a nucleic acid molecule to which the molecular beacon binds is plotted against the concentration to establish a curve. If then the signal obtained with the double-stranded nucleic acid molecule formed by the RNA species and the single-stranded portion of the molecular beacon is measured, it can be matched with the corresponding datapoint on the standard curve, thereby providing the information on the concentration of the RNA species which is equimolar with that of the molecular beacon.

The molecular beacon assay may also be used to determine the integrity of the RNA species by contacting the RNA species with at least two different molecular beacons, wherein the single-stranded portion of each of the at least two molecular beacons is complementary to a different part of the sequence of the at least one RNA species. Hence, a first double-stranded nucleic acid molecule is formed between the single-stranded portion of the first molecular beacon and a first part of the sequence of the at one RNA species and a second double-stranded nucleic acid molecule is formed between the single-stranded portion of the second molecular beacon and a second part of the sequence of the at one RNA species. The amount of each of the double-stranded nucleic acid molecules can be determined as described above by using a standard curve for each of the nucleic acid sequences to which the single-stranded portion of each molecular beacon binds. If the amount of the first double-stranded nucleic acid molecule is substantially the same as the amount of the second double-stranded nucleic acid molecule, the RNA species is considered to have integrity.

Preferably, the single-stranded portions of the first and second molecular beacons bind to opposite ends of the RNA species, such as the 5' end of the RNA species and the 3' end of the RNA species. If the analysis is independent of the target sequence, the first and second nucleic acid probe preferably bind to sequences located 5' of the target sequence and 3' of the target sequence, such as a sequence in the 5' untranslated and the 3' untranslated region, if the target sequence is a coding sequence.

The contacting of the RNA species with the at least two different molecular beacons can take place in parallel reactions, so that one part of the sample comprising RNA prepared by in vitro transcription is contacted with the first molecular beacon and another part of said sample is contacted with the second molecular beacon in a separate reaction. In this case, the fluorophore/quencher pair attached to the first and the second molecular beacon can be the same or different.

Alternatively, the integrity of the RNA species can be analyzed in a multiplexed reaction so that the sample comprising RNA prepared by in vitro transcription is contacted with the first and the second molecular beacon in one reaction. In this case, the fluorophore/quencher pair attached to the first molecular beacon has to be different from the fluorophore/quencher pair attached to the second molecular beacon so that the double-stranded nucleic acid molecules formed can be distinguished from each other. Hence, the fluorophore/quencher pairs attached to the first and the second molecular beacon have to be selected so that they do not interfere with each other, i.e. that the spectrum of light emitted by the fluorescent labels does not overlap.

The molecular beacon assay may also be used to analyze a sample comprising a mixture of different RNA species which have been prepared by RNA in vitro transcription. For this analysis said sample is contacted with different nucleic molecular beacons, wherein the single-stranded portion of each molecular beacon has a sequence which is complementary to at least part of the sequence of one RNA species within the sample, but not to sequences of other RNA species within the sample. The molecular beacon which has a single-stranded portion which is complementary to at least part of the sequence of one RNA species within the sample, but not to sequences of other RNA species within the sample is also called "corresponding molecular beacon" wherein the correspondence relates to the RNA species for which the molecular beacon is specific.

For each of the RNA species present within said sample at least one molecular beacon is used. Hence, if a sample comprises n different RNA species, the analysis is performed with at least n different molecular beacons. If the analysis involves determining the presence and/or the quantity of each of the RNA species within the sample, the analysis is performed with n different molecular beacons. If the analysis involves determining the integrity of each of the RNA species within the sample, the analysis is performed with y×n molecular beacons, wherein y is the number of molecular beacons for one RNA species and is preferably 2.

The contacting of the different RNA species with the corresponding molecular beacons can take place in parallel reactions, so that one part of the sample comprising the mixture of RNA species is contacted with a molecular beacon corresponding to a first RNA species and another part of said sample is contacted with a molecular beacon corresponding to a second RNA species in a separate reaction. In this case, the fluorophor/quencher pair attached to the first and the second molecular beacon can be the same or different. Preferably, the fluorophore/quencher pair attached to the first and the second molecular beacon is the same.

Alternatively, the different RNA species can be analyzed in a multiplexed reaction so that the sample comprising the mixture of RNA species is contacted with the molecular beacons corresponding to each of the RNA species in one reaction. In this case, the fluorophore and/or the quencher attached to the different molecular beacons have to be different so that the double-stranded nucleic acid molecules formed can be distinguished from each other.

As discussed above, the analysis of the RNA species may be independent of the target sequence of these species. In this case, each of the RNA species preferably comprises a synthetic sequence or tag which is located 5' or 3' of the target sequence of the RNA species. The synthetic sequence has to be selected such that the single-stranded portion of the molecular beacon which is intended to detect the corresponding RNA species within the sample binds only to the synthetic sequence of that RNA species, but not to the synthetic sequence of other RNA species within the mixture. Hence, the synthetic sequences have to be sufficiently different from each other to avoid the binding of the molecular beacons to multiple synthetic sequences. For the same reason, the synthetic sequences also have to be sufficiently different from the target sequence of each of the RNA species within the mixture.

In other embodiments the nucleic acid probe may be directed to an element which is naturally present within the 5' or 3' UTR of the RNA species and has not been inserted for detection purposes, but to have an effect on the transcribed RNA molecule. In this case, the different RNA species have to comprise different 5' or 3' UTRs to enable the detection.

In still another embodiment a sample comprising in vitro transcribed RNA may be analyzed by reverse transcription followed by quantitative PCR (RT-qPCR), wherein the analysis is independent of the target sequence.

The RT-qPCR assay may comprise the following steps:
a) contacting a sample comprising in vitro transcribed RNA with at least one primer for reverse transcription under conditions sufficient for reverse transcription, thereby providing a sample containing cDNA corresponding to the at least one RNA species;
b) contacting the sample containing cDNA with at least one set of PCR primers under conditions sufficient for PCR amplification of the cDNA, wherein each PCR primer binds specifically to a part of the cDNA; and
c) detecting the amplified DNA.

The cDNA prepared by reverse transcription corresponds to the RNA species within the sample in that the sequence of the cDNA is complementary to the sequence of the at least one RNA species within the sample.

The skilled person knows conditions which are sufficient for reverse transcription to occur. The RNA is typically incubated with a reverse transcriptase, at least one primer and deoxynucleotides in a suitable buffer at a temperature of 42° C. for one hour. The primer(s) used for reverse transcription may be random, for example hexanucleotides with a random sequence or an oligo(dT) primer hybridizing to the poly(A) stretch of mRNA, or may be target specific.

After the reverse transcription step or simultaneously thereto the cDNA is amplified in a quantitative PCR reaction as defined above. The primers used for the PCR reaction are selected such that they bind to a part of the sequence of the cDNA corresponding to the RNA species so that this part is amplified in the PCR reaction.

The primers may bind to a cDNA sequence corresponding to the target sequence of the at least one RNA species or a part thereof, so that the analysis is dependent on the target sequence of the RNA species. Alternatively and preferably, the primers may bind to a cDNA sequence corresponding to a sequence of the at least one RNA species which is not located within the target sequence, but 5' or 3' thereof. In this case, the analysis is independent of the target sequence of the at least one RNA species.

For determining the quantity of the at least one RNA species in RT-qPCR, the fluorescence signal obtained by amplification of known concentrations of the sequence to be amplified is plotted against the number of cycles needed to amplify a known amount of the sequence to be amplified. If then the fluorescence signal obtained by PCR amplification of the cDNA corresponding to the at least one RNA species is measured, it can be matched with the corresponding datapoint on the standard curve, thereby providing the information on the concentration of the cDNA which is proportional to that of the at least RNA species.

The RT-qPCR may also be used to determine the integrity of the RNA species by contacting the cDNA corresponding to the at least one RNA species with at least two different primer sets, wherein each of the at least two primer sets binds to and amplifies a different part of the cDNA sequence corresponding to the at least one RNA species, leading to two different PCR products corresponding to the different parts of the cDNA sequence. The amount of each PCR product can be determined as described above by using a standard curve for each of the target sequence. If the amount of the first PCR product is substantially the same as the amount of the second PCR product, the corresponding RNA species is considered to have integrity.

Preferably, the first and second primer sets bind to opposite ends of the cDNA corresponding to the at least one RNA species, such as the 5' end of the cDNA and the 3' end of the cDNA. If the analysis is independent of the target sequence, the first and second primer sets preferably bind to cDNA sequences located 5' of the sequence corresponding to the target sequence and 3' of the sequence corresponding to the target sequence, such as a sequence in the 5' untranslated and the 3' untranslated region, if the target sequence is a coding sequence.

The PCRs with the at least two different primer sets can take place in parallel reactions, so that one part of the sample comprising cDNA corresponding to the at least one RNA species is amplified using the first primer set and another part of said sample is amplified using the second primer set in a separate reaction. In this case, the fluorescent label used for detecting and quantifying the PCR products may be the same in both reactions.

Alternatively, the integrity of the RNA species can be analyzed in a multiplexed reaction so that the sample comprising cDNA corresponding to the at least one RNA species is amplified with the first and the second primer set in one reaction. In this case, fluorescent dyes which bind unspecifically to any double-stranded DNA such as SYBR® Green cannot be used. Instead, it is necessary to use primer sets or probes which are labeled with different fluorescent dyes to distinguish between the different cDNAs. Suitable techniques for multiplex quantitative PCR analysis include the Taqman® and the LightCycler® technology.

The Taqman® technology involves the use of a primer pair which is not labeled together with a fluorescent dye and a sequence-specific probe which contains a fluorescent dye attached to one end of the sequence, preferably the 5' end, and a quencher dye at the other end of the sequence, preferably the 3' end. When the probe is intact, the quencher dye reduces or eliminates the fluorescence emitted by the fluorescent dye by fluorescence resonance energy transfer (FRET). If the target sequence is present, the probe anneals downstream from one of the primer binding sites and is cleaved by the 5' nuclease activity of the Taq DNA polymerase as the primer is extended. This cleavage of the probe separates the fluorescent dye from the quencher dye so that the fluorescence emitted by the fluorescent dye increases. Further, the cleavage removes the probe from the target strand, allowing primer extension to continue to the end of the target strand. In each amplification cycle the process of cleavage of the fluorescent probe occurs so that the amount of fluorescence increases proportional to the amount of the amplified target sequence. For multiplex amplification different probes labeled with different fluorescent dye/quencher dye combinations can be used so that the amplification of different sequences can be monitored in one reaction.

In the LightCycler® system a pair of single-stranded oligonucleotides labeled with fluorescent dyes. The first oligonucleotide is labeled at the 3' end with a donor reporter and the second oligonucleotide is labeled at the 5' end with an acceptor reporter. Additionally, the 3' hydroxyl group of the second oligonucleotide is blocked with a phosphate group. The two oligonucleotides hybridize to their target sequence, leaving a space of one to five nucleotides between the probes. When both probes hybridize to the complementary DNA, the donor dye comes into close proximity to the acceptor dye and transfers energy by FRET to the acceptor dye when excited by light. The emission wavelength of the acceptor reporter is detected, wherein the increase in the fluorescence signal is directly proportional to the amount of target DNA.

Useful fluorescent dyes for multiplex quantitative PCR analysis include 6-FAM™, JOE™, TET™, Cal Fluor® Gold 540, HEX™, Cal Fluor® Orange 560, TAMRA™, Cyanine 3, Quasar® 570, Cal Fluor® Red 590, ROX™, Texas Red™, Cyanine 5, Quasar*670 and Cyanine 5.5. Useful quencher dyes for quantitative PCR analysis include BHQ-1, TAMRA, BHQ-2 and BHQ-3.

The RT-qPCR may also be used to analyze a sample comprising a mixture of different RNA species which have been prepared by RNA in vitro transcription. For this analysis the sample comprising cDNA corresponding to the different RNA species is contacted with different primer sets, wherein each primer set is capable of amplifying the cDNA corresponding to one RNA species within the sample, but not the cDNA corresponding to other RNA species within the sample.

For each of the cDNAs corresponding to one RNA species at least one primer set is used. Hence, if a sample comprises n different RNA species, the analysis is performed with at least n different primer sets. If the analysis involves determining the presence and/or the quantity of each of the RNA species within the sample, the analysis is performed with n different primer sets. If the analysis involves determining the integrity of each of the RNA species within the sample, the analysis is performed with y×n primer sets, wherein y is the number of nucleic acid probes for one RNA species and is preferably 2.

The amplification of the cDNAs corresponding to the different RNA species can take place in parallel reactions, so that one part of the sample comprising the mixture of cDNAs is contacted with a primer set capable of amplifying the cDNA corresponding to a first RNA species and another part of said sample is contacted with a primer set capable of amplifying the cDNA corresponding to a second RNA species in a separate reaction. In this case, the fluorescent label used for detecting and quantifying the PCR products may be the same in both reactions and may be a fluorescent label which binds to any double-stranded DNA.

Alternatively, the different cDNAs corresponding to different RNA species can be analyzed in a multiplexed reaction so that the sample comprising the mixture of cDNAs is contacted with the primer sets capable of amplifying the different cDNAs in one reaction. In this case, it is necessary to use primer sets or probes which are labeled with different fluorescent dyes to distinguish between the different cDNAs. The fluorescent dyes have to be selected so that they do not interfere with each other, i.e. that the spectrum of light emitted by the fluorescent dyes does not overlap. The techniques used for multiplex PCR analysis include the Taqman® and the LightCycler® technology as described in detail above.

As discussed above, the analysis of the RNA species may be independent of the target sequence of these species. In this case, each of the RNA species preferably comprises a synthetic sequence or tag which is located 5' or 3' of the target sequence of the RNA species. The synthetic sequence has to be selected such that the primer set which is intended to amplify the cDNA corresponding to an RNA species binds only to the synthetic sequence of that cDNA, but not to the synthetic sequence of other cDNAs within the mixture. Hence, the synthetic sequences have to be sufficiently different from each other to avoid the binding of the primer sets to multiple synthetic sequences. For the same reason, the synthetic sequences also have to be sufficiently different from the target sequence of each of the RNA species within the mixture.

In other embodiments the primer sets may be directed to an element which is naturally present within the 5' or 3' UTR of the RNA species and has not been inserted for detection purposes, but to have an effect on the transcribed RNA molecule. In this case, the different RNA species have to comprise different 5' or 3' UTRs to enable the detection.

Before the sample comprising RNA prepared by in vitro transcription is subjected to the analysis of the present invention, it is preferably purified to remove the components of the RNA in vitro transcription reaction. A suitable purification method is reversed-phase HPLC, preferably as described in WO 2008/077592 A1.

In addition or alternatively to the methods described above, other methods for characterizing samples of in vitro transcribed RNA may be used. These methods include electrophoresis, HPLC, anion exchange chromatography, RNA sequencing, Northern blot, oligonucleotide mapping, microarray analysis, spectrometric methods and mass spectrometry.

Electrophoresis

In those cases where the mRNA mixture is composed of mRNA species with different sizes, electrophoresis may be used to detect respective mRNA species in a mixture and also to quantify said mRNA species. Electrophoretic methods have certain limitations in terms of resolution etc. that are known to a person skilled in the art.

The most often used electrophoretic technique in RNA analysis is gel electrophoresis. RNA molecules are negatively charged; therefore RNA molecules migrate toward the anode in the presence of electric current. Various non-crosslinked matrixes including polyacrylamide, cellulose derivatives, agarose derivatives and polyvinylpyrrolidone can be used as sieving polymers to separate RNAs of different sizes. Therefore, such a method is suitable for the analysis of mRNA mixtures comprising mRNA species of different sizes. Because mass is approximately related to chain length of the RNA, the length of an RNA molecule is more generally determined by its migration in the polymer. For most applications involving RNAs of less than or equal to 600 nucleotides, denaturing acrylamide gels are most appropriate. In contrast, agarose gels are generally used to analyze RNAs of more than 600 nucleotides, and are especially useful for analysis of mRNAs (e.g., by Northern blotting).

Alternatively, capillary electrophoresis may be used. Capillary electrophoresis works on similar principles than gel electrophoresis. Capillary electrophoresis (CE) offers high-resolution separation of ionic analytes due to efficient heat dissipation. Typically, CE is performed in fused silica capillaries but may also be performed in glass or plastic chips. Ionization of silanol groups results in generation of electroosmotic flow that is detrimental to high resolution separations and has to be suppressed by introducing static or dynamic coating. DNA/RNA is usually denatured with urea, formamide, methyl formamide, dimethyl formamide, ethyl formamide, and dimethyl sulfoxide. Proteins can be denatured with sodium dodecyl sulfate, lithium dodecyl sulfate, sodium lauroyl sarcosinate, sodium decyl sulfate, lauric acid, urea, thiourea, formamide, methyl formamide, dimethyl formamide, ethyl formamide, dimethyl sulfoxide. Analytes separated by capillary electrophoresis can be detected online by various detection techniques. UV absorption and laser-induced fluorescence of fluorescently labeled analytes are the most frequently used detection techniques in capillary electrophoresis.

In general, electrophoretic analysis of RNA provides information regarding RNA length and therefore about the identity in embodiments where RNA species of different sizes are present in the RNA mixture. Additionally, electrophoresis may also be suitable to quantify RNA and to gain information about the integrity of an RNA species. However, if RNA mixtures containing RNA species of similar size are to be analyzed, electrophoresis is not sufficient to discriminate said mRNA species.

HPLC:

In embodiments where the mRNA mixture is composed of mRNA species with different sizes, HPLC may be used to detect respective mRNA species in a mixture and also to quantify said mRNA species. High-performance liquid chromatography (HPLC; formerly referred to as high-pressure liquid chromatography), is a technique in analytic chemistry used to separate the components in a mixture, to identify each component, and to quantify each component. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column.

HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power when separating mixtures, which is why it is a popular chromatographic technique.

An HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

Under certain conditions, HPLC can be used to analyze mRNA mixtures. For example, ion-pair reversed-phase high performance liquid chromatography (IP RP HPLC) technology under fully denaturing conditions has been applied for RNA analysis. This technology can be applied to qualification (integrity measure), quantification and purification of a wide range of labeled/unlabeled RNA samples, such as mRNA, rRNA and total RNA. However, the respective mRNA species have to differ in size, so that the retention times of the RNA species differ and the HPLC profiles of the respective RNA species do not overlap. In the context of analyzing highly similar RNA sequences (e.g., a polyvalent mRNA mixture wherein mRNA species are very similar in size), the analysis of said mixtures via HPLC is currently not possible.

Anion exchange (AEX) chromatography is a method of purification and analysis that leverages ionic interaction between positively charged sorbents and negatively charged molecules. AEX sorbents consist of a charged functional group (e.g. quaternary amine, polyethylenimine, diethylaminoethyl, dimethylaminopropyl etc.), cross-linked to solid phase media. There are two categories of anion exchange media, "strong" and "weak" exchangers. Strong exchangers maintain a positive charge over a broad pH range, while weak exchangers only exhibit charge over a specific pH range. Anion exchange resins facilitate RNA capture due to the interaction with the negatively charged phosphate backbone of the RNA providing an ideal mode of separation. The mechanism of purification or analysis can involve binding the RNA under relatively low ionic strength solution to an AEX sorbent.

Loading conditions for the AEX chromatography can include non-denaturing conditions with or without the addition of chaotropic salts as well as denaturing conditions which can or cannot include the use of chaotropic agents. Thermal and chemical denaturation is the preferred method of denaturing the RNA for analytical purposes. AEX chromatography materials can include weak resins. Weak resins include resins that have a low affinity for polypeptides and a high affinity for polynucleotides, e.g., RNA transcripts. Furthermore, weak resins also include resins that have a low affinity for polypeptides and a low affinity for polynucleotides, e.g., RNA transcripts. AEX chromatography materials can also include porous IEX media: polystyrene divinylbenzene, polymethacrylate, crosslinked agarose, allyl dextran/N—N-bis acylamide, or silica, for example. In one embodiment, non-porous IEX media such as monolithic columns can be used. In another embodiment, membrane-based ion exchangers are used, including Millipore chromasorb and Sartorius sartobind.

In some embodiments, AEX chromatography conditions can include strong or weak anion exchange groups, mixed mode, heated or unheated conditions, denaturing or non-denaturing conditions, various particle/pore sizes, pH range between 3 and 9. In other embodiments, chaotropic salts are used, such as urea, perchlorate, and guanidinium salts. Examples of mobile phase compositions include the entire Hofmeister series of ions, salts such as chlorine, bromine, citrate, iodide, sulfate, phosphate, perchlorate, and counterions/cations such as sodium, potassium, and calcium. Additives/modifiers to the mobile phase can include organics such as ethanol, acetonitrile, and IPA. In some embodiments, the buffer comprises Tris, HEPES, or phosphate.

In some embodiments, the RNA transcript is denatured before undergoing AEX, using >6 M urea (preferably >7 M urea), and heating the RNA transcript to >70° Celsius for about 5 minutes. The RNA transcript is then contacted with an ion exchange sorbent with a positively-charged functional group linked to solid phase media. The RNA transcript sample is delivered with a mobile phase, so that the RNA transcript binds the positively-charged functional group of the ion exchange sorbent.

In one embodiment, the mobile phase is a Tris-EDTA-acetonitrile buffered mobile phase. In another embodiment, there are two mobile phases that include Tris-EDTA-acetonitrile buffer. In a further embodiment, the mobile phase contains a strong chaotropic salt, such as sodium perchlorate. Next, the RNA transcript and any impurities are eluted from the ion exchange sorbent. The RNA transcript and any impurities are then analyzed. The analysis can include analysis of charge heterogeneity of the RNA transcript, mass heterogeneity of the RNA transcript, process intermediates, hybridization impurities, and degradation products.

Next generation Sequencing/RNA Sequencing:

DNA sequencing is the process of determining the precise order of nucleotides within a DNA molecule. It includes any method or technology that is used to determine the order of the four bases—adenine, guanine, cytosine, and thymine—in a strand of DNA. It includes Maxam-Gilbert sequencing, Sanger sequencing (chain-termination sequencing), next generation sequencing, cycle sequencing, capillary electrophoresis DNA sequencing, single-molecule real-time sequencing, Ion Torrent sequencing, pyrosequencing, sequencing by synthesis, sequencing by ligation.

To sequence RNA, the usual method is first to reverse transcribe the respective sample to generate cDNA fragments. By sequencing the cDNA, the sequence of the RNA transcript can be determined. The obtained cDNA fragments can be sequenced with common methods known in the art (see above), preferably with next-generation sequencing (NGS).

The term "next generation sequencing" (also often termed "massively parallel sequencing") refers to a variety of related technologies including "Roche 454", Helicos, Pacific Biosciences and Life Technologies (ABI). Other sequencing methods include CAGE tag-sequencing, deep sequencing, bidirectional sequencing, RNA sequencing, shotgun sequencing, bridge PCR, massively parallel signature sequencing (MPSS), polony sequencing, pyrosequencing, Illumina (Solexa) sequencing SOLiD sequencing, ion semiconductor sequencing, DNA nanoball sequencing, heliscope single molecule sequencing, and single molecule real time (SMRT) sequencing.

Compared to traditional sequencing methods (e.g., Sanger Sequencing), NGS produces very large numbers of simultaneous (short) sequence reads that have to be assembled to a reference (e.g., the mRNA that has to be detected). NGS techniques allow for a precise detection and quantification of very similar sequences in a mixture, however, a major drawback is the fact that RNAs have to be reversely transcribed before sequencing occurs which may bias the results (reverse transcriptases are error-prone). Moreover, the analysis of NGS data still requires substantial computational and bioinformatical resources. Especially in the context of analyzing highly similar RNA sequences (e.g., polyvalent mRNA mixture), the analysis of NGS data may be challenging.

Northern Blots:

In certain embodiments, RNA mixtures are analyzed via northern blotting. After separating RNA molecules based on electrophoresis, RNA molecules in the gel are transferred to a nylon or nitrocellulose membrane by capillary transfer. An RNA of interest can be identified by hybridization to radioactive or chemiluminescent probes and detected by autoradiography or photography. Gels stained with EtBr allow observation of quality and quantity of RNA prior blotting. Absolute quantitation can be performed by comparing the signal to a standard curve generated using known amounts of an in vitro transcript corresponding to the target RNA. Compared to RT-PCR Northern blotting has a low sensitivity, but has a high specificity.

Oligonucleotide Mapping:

Oligonucleotide mapping involves incubating an RNA transcript with multiple polynucleotide (DNA or RNA) probes under conditions allowing the hybridization of the probes to the RNA transcript to form duplexes along different regions of the RNA transcript. In one embodiment, the probes are antisense probes. In another embodiment, the probes are 10-40 nucleotides in length. In a further embodiment, the probes are 15-30 nucleotides in length. In another embodiment, the probes are less than about 20 nucleotides in length, and at least 8 of those nucleotides are deoxyribonucleotides. In another embodiment, the probes are complementary to the 3' end of the RNA immediately upstream of the poly-A tail. The probes can be dispersed throughout the RNA transcript, binding at regions less than about 50 nucleotides apart on the RNA transcript.

After the duplexes have formed, an RNase is added under conditions sufficient to allow the RNase to digest portions of the duplexes along the RNA transcript, forming RNA fragments. The RNase can be any RNase that can cleave such duplexes, such as RNase H or RNase T1. The fragment mRNA can then be characterized by HPLC coupled to mass spectrometry (MS; see below).

Mass Spectrometry:

In certain embodiments, mass spectrometry based methods may be applied to analyze mRNA mixtures. Mass spectrometry is an analytical technique that provides structural and molecular mass and/or concentration information on molecules after their conversion to ions.

It is performed using a mass spectrometer which includes an ion source for ionizing the fractionated sample and creating charged molecules for further analysis. For example ionization of the sample can be performed by electrospray ionization (ESI), atmospheric pressure chemical ionization (APCI), photoionization, electron ionization, fast atom bombardment (FAB)/liquid secondary ionization (LSIMS), matrix assisted laser desorption/ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc. The molecules are first ionized to acquire positive or negative charges and then they travel through the mass analyzer to arrive at different areas of the detector according to their mass-to-charge ratio.

Suitable analyzers for determining mass-to-charge ratios include quadropole analyzers, ion traps analyzers, and time-of-flight analyzers. The ions can be detected using several detection modes. For example, selected ions can be detected (i.e., using a selective ion monitoring mode (SIM)), or alternatively, ions can be detected using a scanning mode, e.g., multiple reaction monitoring (MRM) or selected reaction monitoring (SRM).

The sequence and composition of small oligonucleotides (<30 nt) can be determined by LC-MS (liquid chromatography-tandem mass spectrometry) or RT-qPCR sequencing. Mass spectrometry of large mRNA has been difficult since mRNA is highly charged and generates a broad mass envelop in electrospray-MS that is difficult to deconvolute, and it is difficult to differentiate missing or modifications in one or a few nucleotides out of hundreds to thousands of nucleotides.

Mass spectrometry has both qualitative and quantitative uses. These include identifying unknown compounds, determining the isotopic composition of elements in a molecule, and determining the structure of a compound by observing its fragmentation. Other uses include quantifying the amount of a compound in a sample.

A common combination of separation techniques with mass spectrometry is gas chromatography-mass spectrometry (GC-MS). Similar to GC-MS, is liquid chromatography-mass spectrometry (LC-MS), which separates compounds chromatographically before they are introduced to the ion source and mass spectrometer. It differs from GC-MS in that the mobile phase is liquid, usually a mixture of water and organic solvents, instead of gas.

Capillary electrophoresis-mass spectrometry (CE-MS) is a technique that combines the liquid separation process of capillary electrophoresis with mass spectrometry. Ion mobility spectrometry-mass spectrometry (IMS/MS or IMMS) is a technique where ions are first separated by drift time through some neutral gas under an applied electrical potential gradient before being introduced into a mass spectrometer. Drift time is a measure of the radius relative to the charge of the ion. The duty cycle of IMS (the time over which the experiment takes place) is longer than most mass spectrometric techniques, such that the mass spectrometer can sample along the course of the IMS separation. This produces data about the IMS separation and the mass-to-charge ratio of the ions in a manner similar to LC/MS. The duty cycle of IMS is short relative to liquid chromatography or gas chromatography separations and can thus be coupled to such techniques, producing triple modalities such as LC/IMS/MS.

Microarrays:

In certain embodiments, mRNA mixtures may be analyzed using microarray based methods.

The principle of DNA microarray technology is based on the fact that complementary sequences of DNA/RNA can be used to hybridize immobilized DNA molecules. This involves three major multi-stage steps. First, the manufacturing of microarrays, which involves the availability of a chip or a glass slide with its special surface chemistry, the robotics used for producing microarrays by spotting the DNA (targets) onto the chip or for their in situ synthesis. Second, the sample preparation and array hybridization step. The last step comprises image acquisition and data analysis. This step involves microarray scanning, and image analysis using sophisticated software programs that allows us to quantify and interpret the data.

The microarray procedure can be divided into two main parts. First, a collection of microscopic DNA spots are attached onto a solid surface, such as glass, plastic or silicon chip forming an array. The immobilized DNA segments of identified sequenced genes are known as probes, thousands of which can be used in a single DNA microarray, covering almost every gene in a genome. Following, in a hybridization step fluorescently labeled cDNA molecules, prepared from mRNA converted into cDNA from a sample of interest and labeled with a different tracking molecules, i.e. fluorescent cyanine dyes, hybridize to the known sequences immobilized on the solid support. After the hybridization step, the spots in the hybridized microarray are excited by a laser and scanned at suitable wavelengths to detect the fluorescent dyes. The amount of fluorescence emitted upon excitation corresponds to the amount of bound nucleic acid. The signal collected from each spot is used to estimate the expression level of a distinct gene.

Spectrrometric Methods:

In certain embodiments, spectrometric methods may be used to analyze mRNA mixtures. Ultraviolet (UV) absorbance can be used to measure RNA concentration, whereby the main wavelengths of interest are 260 nm, 280 nm, 230 nm. Absorbance at 260 nm is used to measure the amount of nucleic acid present in a sample, the concentration can be calculated using the 260 nm reading and a conversion factor based on the extinction coefficient for RNA (e.g. $A_{260}$ of 1.0=40 sg/ml RNA). Determining RNA quality, the ration between the absorbance values at A260 and A280 gives an indication for RNA purity with respect to contaminants that absorb in the UV, such as protein. However, using absorbance lacks specificity as well as sensitivity to quantitate low-level samples. All nucleic acids absorb at 260 nm (ssDNA, dsDNA, RNA) and using this method it is not possibly to distinguish between various forms of nucleic acid. Also, if amounts of contaminants that absorb also at 260 nm are present in a sample, the contaminants themselves can contribute to the absorbance value, leading to an overestimation of nucleic acid concentration. In addition, changes in RNA integrity are not reflected by this measurement, as single nucleotides will also contribute to the 260 nm reading.

An alternative way to assess RNA concentration is to measure the fluorescence intensity of dyes that specifically bind to nucleic acids and selectively emit light when bound. This method enables sensitive quantitation of small amounts of RNA that cannot accurately be assessed with spectrophotometry. Fluorescence can be quantified with a fluorescence photometer.

The method of the present invention can be used for the quality control of RNA produced by in vitro transcription, in particular of mixtures of different RNA species. This quality control preferably includes determining both the presence, quantity and integrity of RNA. As discussed above, such a quality control is particularly important in the production of RNA which is to be used for administration to humans or animals, for example for therapeutic purposes. If the RNA or mixture of different RNA species shows the required quality in terms of identity of the RNA(s), quantity of each of the RNA species in the sample and integrity, the sample can be processed further to be ultimately administered to a human or animal subject. If any of the criteria identity, quality and integrity is not met, the RNA sample will be discarded, as it is not suitable for administration to humans or animals.

The present invention also relates to an expression vector comprising in 5' to 3' direction a promoter and operably linked thereto a nucleic acid sequence encoding a target sequence and at least one synthetic sequence located 5' and/or 3' of the target sequence.

As described above, such an expression vector can be used for the production of RNAs which can be analyzed independent of their target sequence.

In another embodiment the present invention relates to an expression vector comprising in 5' to 3' direction a promoter and operably linked thereto a nucleic acid sequence encoding a 5' untranslated region, a multiple cloning site and a nucleic acid encoding a 3' untranslated region, wherein the 5' and/or 3' untranslated region comprises a synthetic sequence.

The multiple cloning site of this expression vector can be used to insert different coding sequences, thus enabling the production of different target sequences having the same nucleic acid tag attached. Accordingly, the same nucleic acid probe for use in a nuclease protection assay, molecular beacon and/or primer set can be used to analyze different RNAs, as they bind to the synthetic sequence which is present in all these RNAs. The skilled person will appreciate that the expression vector can only be used in combination with target sequences which do not comprise a sequence which is sufficiently complementary to the nucleic acid probe, the molecular beacon or the primer set to bind these nucleic acid sequences.

EXAMPLES

The following examples are intended to illustrate the invention in a further way. They are merely illustrative and not intended to limit the subject matter of the invention.

Example 1: Preparation of DNA Encoding HA Proteins of Several Serotypes

DNA sequences encoding different hemagglutinin (HA) proteins were generated. Hemagglutinin is a glycoprotein found on the surface of influenza viruses (Influenza A and Influenza B). HA proteins of various serotypes were used as indicated in Table 1. The DNA sequences were prepared by modifying the wild type encoding DNA sequence to optimize the GC content for stabilization. Sequences were introduced into a pUC19 derived vector together with a 5'-UTR derived from the 32L4 ribosomal protein (32L4 TOP 5'-UTR) and a 3'-UTR derived from albumin, a histone-stem-loop structure, and a stretch of 64 adenosines at the 3'-terminal end.

The obtained plasmid DNA constructs were transformed and propagated in bacteria (*Escherichia coli*) and plasmid DNA was isolated and used e.g. for the subsequent cloning of molecular beacon-tags into the plasmids (see Example 2)

TABLE 1

| GC optimized HA coding sequences (cds) used in the experiments (RNA) | |
| --- | --- |
| HA protein description | SEQ ID NO GC optimized RNA |
| H3N2 Influenza A virus (Texas/2012) | 1 |
| H1N1 Influenza A virus (California/2009) | 2 |
| HA Influenza B virus (Massachusetts/2012) | 3 |
| HA Influenza B virus (Brisbane/2008) | 4 |

Example 2: Design of Coding Sequence
Independent Molecular Beacon Probes and Tags The RNAs that are produced by RNA in vitro transcription using templates according to Example 1 are very similar in size and sequence. This similarity would largely impede the design of coding-sequence specific molecular beacon probes that reliably distinguish between the four RNA species in a RNA mixture containing these four RNA species.

Therefore, the goal of the present experiment was to design coding-sequence independent molecular beacon probes and corresponding tags to facilitate and streamline the detection of a specific RNA species in a mixture of very similar RNA species. Four coding sequence independent molecular beacons probes have been designed based on best-design principles (optimal stem-and-loop structure) according to methods and tools known in the art (e.g., www.molecular-beacons.org/PA design.html; "Design and optimization of molecular beacon real-time polymerase chain reaction assays." (In Herdewijn, P. (ed.); Beacon Designer (Premier Biosoft International)). The structure of the beacon probes were assessed using in silico structure predictions (e.g., mfold web server; see FIG. 2).

In addition, the beacons were analyzed for the presence of endonuclease restriction sites. The obtained sequences were reverse transcribed in silico. The reverse complementary beacon probe sequences where then aligned to the mixture of RNA sequences (four HA antigens, see Example 1) to characterize for potential off-target effects in silico. The final best-design beacon probes are listed in Table 2.

TABLE 2

| Beacons used in the experiment; stem region in bold; loop region underlined; all beacons have Cy3 attached to the 5' end as a fluorophore and BHQ attached to the 3' end as a quencher | | |
| --- | --- | --- |
| SEQ ID | Beacon | DNA Sequence |
| 5 | CU | CGAGGTGTTGAAGAGAAGTTGCTTGTCCTCG |
| 6 | FR | CGAGGTTCCGAGCTAACTGTATTTCTCCTCG |
| 7 | NU | CGAGGAACTGATGTCTTGAAATTAACCCTCG |
| 8 | SP | CGAGGTCTCCTATTAATGCTTGTCACCCTCG |

Example 3: Cloning of Plasmid Vectors Containing
a Beacon Tag in the 3' UTR

The goal of the experiment was to clone beacon recognition sites ("beacon tags") that will be recognized by the designed molecular beacon probes into the 3' UTRs of corresponding HA expression vectors (the 3' end of the 3' UTR region: SEQ ID NO. 9). The beacon tags were inserted 5' of the stem loop (5' of "AAA" motif) and 3' of the poly C region elements present in the 3' UTR of the expression vector (see below).

```
>SEQ ID NO. 9:
3' end of the 3' UTR located on the corresponding expression
vectors:

AAAAAAAATGCATCCCCCCCCCCCCCCCCCCCCCCCCCCCCCCCCCAAAggctc tTTTCagagccACCAGAATTC (underlined: 65 nt, relevant for oligo synthesis NsiI restriction site: ATGCAT EcoRI restriction site (bold): G'AATTC stem loop (small letters): ggctct; agagcc Poly-C region: italics
```

1. Primer Design:

Primers were designed containing an ▓▓ restriction site (forward primers) and an EcoRI (in bold) restriction site

TABLE 3

```
Forward ("fw") and reverse ("rev") PCR primers used in the experiment;
beacon tag regions are underlined; restriction sites are highlighted.

SEQ   Primer
ID    ID

10    CU fw    GTCCTCATGCATCCCCCCCCCCCCCCCCCCCCCCCCCCCCCCC

ACAAGCAACTTCTCTTCAACA

11    CU       catggtGAATTCTGGTGGCTCTGAAAAGAGCCttTGTTGAAGAG
      rev      AAGTTGCTTGT 12    FR fw    GTCCTCATGCATCCCCCCCCCCCCCCCCCCCCCCCCCCCCCCC

AGAAATACAGTTAGCTCGGAA

13    FR       catggtGAATTCTGGTGGCTCTGAAAAGAGCCtttTTCCGAGCTAA
      rev      CTGTATTTCT

14    NU       GTCCTCATGCATCCCCCCCCCCCCCCCCCCCCCCCCCCCCCCC fw       GTTAATTTCAAGACATCAGTT

15    NU       catggtGAATTCTGGTGGCTCTGAAAAGAGCCtttAACTGATGTCT
      rev      TGAAATTAAC 16    SP fw    GTCCTCATGCATCCCCCCCCCCCCCCCCCCCCCCCCCCCCCCC

GTGACAAGCATTAATAGGAGA

17    SP rev   catggtGAATTCTGGTGGCTCTGAAAAGAGCCtttTCTCCTATTAA
                TGCTTGTCAC
```

2. PCR Amplification and Cloning:

Primers pairs listed in Table 3 were used to generate short dsDNA fragments (PCR product size 99 base pairs each). 1 μl respective forward (fw) primer (100 μM) and 1 μl respective reverse (rev) primer (100 μM), 25 μl 2× GoTaq® Hot Start Green Mastermix (Promega) and 23 μl nuclease free H₂O were mixed and amplified in a PCR thermocycler. The obtained 99 base pair products were analyzed by agarose gel electrophoresis and PCR products were purified using a QIAquick® PCR purification kit (Qiagen).

1 μg of purified PCR products (beacon tags) were digested using NsiI and EcoRI fast digest enzymes, and cloned into the target plasmids harboring HA antigens (linearized with NsiI and EcoRI) using T4 DNA ligase (according to the manufacturer's instructions; Rapid DNA ligation kit).

2 μl of the respective ligation reactions were used to transform chemically competent DH5alpha bacterial cells. Obtained clones were analyzed via colony PCR, and respective positive clones (harboring the beacon tags) were taken to generate plasmid DNA for further experiments.

The obtained vectors were used to generate mRNA for further experiments (see Example 4).

Example 4: RNA In Vitro Transcription

The DNA plasmids obtained in Example 3 were linearized using EcoRI and transcribed in vitro using DNA dependent T7 RNA polymerase in the presence of a nucleotide mixture under respective buffer conditions. The obtained mRNAs were purified as described in WO 2008/077592 A1.

Example 5: Selective Detection of RNA Target Oligonucleotides Using Molecular Beacons The goal of the experiment was to test whether the beacon recognition sites designed above enable a selective detection (reverse primers) and corresponding beacon recognition sites. The primers used for PCR amplification are shown in Table 3 (SEQ ID NO. 10-17).

via molecular beacons. As a proof-of-principle experiment, target oligonucleotides were used to analyze the specificity of the designed molecular beacon probes. The target RNA oligonucleotides are provided in Table 4 (SEQ ID NO. 18-21).

Experimental Procedure:

100 μM target oligonucleotides (see Table 4) or a mixture thereof were mixed with 5 μM molecular beacon probe in 100 mM Tris/HCl 100 mM NaCl, in a total volume of 100 μl. The reaction was incubated for 5 minutes at 95° C., quickly chilled down to 25° C., and incubated at 25° C. (total incubation time: 40 minutes). The fluorescence signal was determined using a commercially available plate reader. The results are shown in FIG. 3.

TABLE 4

| List of target RNA oligonucleotides | | |
| --- | --- | --- |
| SEQ ID NO | Target Oligo ID | Target oligo sequence |
| 18 | CU target oligo | ACAAGCAACUUCUCUUCAACA |
| 19 | FR target oligo | AGAAAUACAGUUAGCUCGGAA |
| 20 | NU target oligo | GUUAAUUUCAAGACAUCAGUU |
| 21 | SP target oligo | GUGACAAGCAUUAAUAGGAGA |

Results:

FIG. 3 shows that the designed molecular beacon probes specifically detected their target RNA oligonucleotides, but did not detect the non-target RNA oligonucleotides. Moreover, using the molecular beacon approach, it was possible to detect the target RNA nucleotides in a mixture with the other three non-target RNA nucleotides.

In summary, the results of the proof-of-principle experiment show that the assay should also work for the detection of mRNA species harboring molecular beacons designed based on "best-design principles" to detect mRNA species in a target-sequence independent manner via molecular beacon-tag elements. This would enable the specific detection and quantification of mRNA species in an mRNA mixture (see Example 6).

Example 6: Selective Detection and Quantification of HA mRNA Species in a HA mRNA Mixture Using Molecular Beacons The goal of the experiment is to test the inventive molecular beacon assay using HA mRNA species bearing specific molecular beacon tags. For these experiments, HA mRNA is obtained according to Example 4. The molecular beacon assay is performed according to Example 5. Every molecular beacon probe has a certain background fluorescence level (see for example FIG. 3). To quantify mRNA species in mRNA mixtures via molecular beacons, standard curves for each molecular beacon probe have to be generated. This can be performed by titrating defined amounts of target mRNA to the molecular beacon probes. The detected fluorescence can be expressed as fluorescence per µg mRNA. The generated standard curve can be used for the quantification of an mRNA species.

Example 7: S1 Nuclease Assay for the Analysis of RNA Mixtures

The goal of this experiment was to establish an assay based on fluorescently labeled biotinylated DNA oligo probes for the detection and quantification of certain mRNA species in mRNA mixtures. For mRNA synthesis, expression vectors harboring different HA antigens were used (SEQ ID NO 1-4). The RNA in vitro transcription was performed as described in Example 4. The fluorescently labelled coding sequence specific DNA oligo probes used for mRNA detection are listed in Table 5 (SEQ ID NO. 22-33).

TABLE 5

DNA oligo probes used for the S1 assay; all probes carry a 5' Cy3 and a 3' Biotin TEG

| SEQ ID NO | DNA probe ID | Sequence | Target RNA |
|---|---|---|---|
| 22 | S1 | GTCCCACTTCTTGTTCTGGA AGCCGTC | H3N2 (Texas/2012) |
| 23 | S4 | CCAGGAGCTCGCGGTGGACA GGCTCTC | H1N1 (Californica/ 2009) |
| 24 | S8 | ATGGTCGCGAAGAAGCCGCT CT | HA Influenza B (Massachusetts/2012) |
| 25 | S10 | CACGCGGGCGGACGGGATCT TGCCGGT | HA Influenza B (Brisbane/2008) |

1. Hybridization of DNA Probes and RNA Species:

100 pmol of ssDNA probes and 25 pmol of the corresponding target HA mRNA were incubated in 35 µl water for injection at 95° C. to resolve potential secondary structures. Then the temperature of the mixture was slowly reduced to 25° C. For the hybridization experiment, a ssDNA:RNA ratio of 4:1 was chosen to increase the likelihood of probe-target hybridization.

2. RNAse H Digestion of RNA in DNA-RNA-Hybrids:

The goal of this control step was to test the efficiency of probe hybridization using an enzyme (RNAse H) that specifically digests DNA/RNA duplex structures. The reactions obtained from the hybridization step (see below) were digested with 1 U/µl RNAse H in a respective reaction buffer for 30 minutes at 25° C. The resulting RNA fragments were analyzed via agarose gel electrophoresis for an assessment of probe quality (results not shown).

3. S1 Nuclease Digestion:

The probes described in Table 5 were used to analyze an mRNA mixture (4 HA antigens, 25 pmol per RNA species). Each probe (50 pmol) was hybridized with the respective single mRNA species (5 pmol, 15 pmol, 25 pmpl, 50 pmol) and RNA mixtures (25 pmol per mRNA species) in the presence of 0.5 mM Na-EDTA according to the procedure explained above. Following that, DNA-RNA hybrids were treated with an enzyme S1 nuclease. In essence, 1 µl S1 nuclease (5 U/µl; Promega) and 4 µl 10× S1 nuclease reaction buffer (Promega) were added to 35 µl hybridization reactions and incubated for 15 minutes at 25° C. Following that, the reaction was stopped by adding Proteinase K (57.5 µl TBS, pH 7.5; 2.5 µl Proteinase K (29 µg/µl; Peqlab)). The reaction was incubated for 60 minutes at 37° C.

4. RNA-DNA Hybrid Couplin on Streptavidin Coated Plates:

The obtained short biotinylated and fluorescently labeled RNA/DNA hybrids were used for coupling on streptavidin coated plates (Pierce® Streptavidin High binding Capacity coated 96-well plates; Thermo Scientific). The streptavidin coated plates were 3× washed in TBS, pH 7.2 before adding 100 µl of the respective reactions. The plate was incubated for 30 minutes at 37° C. to allow coupling of RNA/DNA hybrids to the plate. Following that, plates were washed 4× with 200 µl TBS-T, pH 7.2. For fluorescence detection, fresh 200 µl TBS, pH 7.2 was added.

5. Fluorescence Detection and Analysis:

Cy3 fluorescence detection was performed using a synergy HT plate reader (BioTek) using respective fluorescence filter sets (absorption 530/25 nm; emission 590/535 nm). Endpoint fluorescence values were recorded. The results are shown in FIG. 4.

6. Results:

The results of the experiment show that the used DNA oligo probes specifically detected their target mRNA. The detected fluorescence signal for each tested experimental setup was concentration dependent; moreover, it was possible to detect and quantify a specific mRNA species in a mixture of four mRNAs. The used controls show that the obtained signals are dependent on the presence of the target RNA sequence (no signal could be detected in settings without target RNA), and that the S1 nuclease treatment was necessary to obtain a specific fluorescence signal.

Summarizing the above, the results of the present experiments showed that the S1 nuclease assay can be used to analyze mRNA mixtures in terms of identity and quantity. In the present experiment, target sequence specific DNA oligo probes were used. Such a setup requires a thorough and time-consuming probe design, and may not be applicable for highly similar RNA mixtures.

Example 8: S1 Nuclease Assay for the Analysis of RNA Mixtures Using Plasmid Encoded Tags The goal of this experiment is to establish a coding sequence independent S nuclease assay for the analysis of RNA mixtures. The plasmids generated in Example 3, harboring distinctive tags (CU, FR, NU, SP), are used to synthetize RNA (according to Example 4). The generated RNA species that harbor distinctive tags in their UTR regions are used to perform the S1 nuclease assay. The S1 nuclease assay is performed according to Example 7, using DNA oligo probes listed in Table 6 (SEQ ID NO. 26-29).

TABLE 6

DNA probes used for the S1 assay; all probes carry a 5' Cy3 and a 3' Biotin TEG

| SEQ ID | ID | DNA Sequence |
|---|---|---|
| 26 | S1_CU | TGTTGAAGAGAAGTTGCTTGT |
| 27 | S1_FR | TTCCGAGCTAACTGTATTTCT |
| 28 | S1_NU | AACTGATGTCTTGAAATTAAC |
| 29 | S1_SP | TCTCCTATTAATGCTTGTCAC |

Example 9: RT-qPCR for the Analysis of RNA Mixtures

The goal of this experiment was to optimize a RT-qPCR for the detection of highly similar HA mRNA species. For RNA synthesis, expression vectors harboring different HA antigens were used (SEQ ID NO 1-4). The RNA in vitro transcription was performed according to Example 4.

1. Primer Design:

Primers specific for their target sequence were designed using a commercially available software package. Primers pairs were chosen that yield PCR products between 70 and 100 base pairs. Respective primer candidates were also analyzed for their off-target binding properties in silico. For example, primer pairs designed for the detection of H3N2 Influenza A (primers SEQ ID NO 30 and 31) were tested for their binding properties on the other three HA mRNAs (H1N1 Influenza A (California/2009), HA Influenza B (Massachusetts/2012), HA Influenza B (Brisbane/2008)). The primers used for the present RT-qPCR experiments are provided in Table 7 (SEQ ID NO. 30-37).

TABLE 7

Primers used for one-step RT qPCR and two-step RT-qPCR

| SEQ | Target | DNA | Sequence |
|---|---|---|---|
| 30 | H3N2 Influenza A (Texas/2012) | fw | CCCATCGGCAAGTGCAA GTC |
| 31 | H3N2 Influenza A (Texas/2012) | rev | CCGGTTCACGTTCTGGAA GG |
| 32 | H1N1 Influenza A (California/2009) | fw | GGAGAAGCGGATCGAGA ACC |
| 33 | H1N1 Influenza A (California/2009) | rev | CGGCGTTGTACGTCCAGA TG |
| 34 | HA Influenza B (Massachusetts/2012) | fw | CCAACCCCCTGACGGTG |
| 35 | HA Influenza B (Massachusetts/2012) | rev | TGTCGCCGTACAGGTTCT TC |
| 36 | HA Influenza B (Brisbane/2008) | fw | CACCCACAACGTGATCA ACGC |

TABLE 7-continued

Primers used for one-step RT qPCR and two-step RT-qPCR

| SEQ | Target | DNA | Sequence |
|---|---|---|---|
| 37 | HA Influenza B (Brisbane/2008) | rev | GTTGCCGTTCGTGATGTT GG |

2. Two-Step RT-qPCR:

In a two-step RT-qPCR, cDNA synthesis and qPCR are performed in different reactions. cDNA synthesis was performed using 100 ng RNA. Moreover, RNA mixtures were generated containing all four RNA species (100 ng each) or RNA mixtures where the target RNA sequence was absent (negative control). The respective RNA solutions were diluted to 0.1 µg/µl in water for injection (WFI).

1 µl random hexamer primers (0.2 µg/µl; Fermentas), 1 µl 10 mM dNTP mix and the respective volume of RNA (e.g., for single RNAs 1 µl; for RNA mixtures 4 µl; for RNA mixtures without target RNA sequence 3 µl) were denatured in a total volume of 14 µl for 5 minutes at 65° C. Then, cDNA synthesis was performed according to the SuperScript III reverse transcriptase manual (Invitrogen). The obtained cDNA in a concentration range of 50 fg/µl to 5 ng/µl was used for RT-qPCR using SsoAdvanced™ Universal SYBR® Green Supermix (Bio-Rad) according to the manufacturer's protocol using respective primers (see Table 7). An exemplary result is shown in FIG. 5.

3. One-Step RT-qPCR:

In a one-step RT-qPCR, cDNA synthesis and qPCR are performed in one reaction, using a iTaq™ Universal SYBR® Green One-Step Kit (Bio-Rad) according to the manufacturer's protocol using respective primers (see Table 7).

Results:

An exemplary result for the two-step RT-qPCR is shown in FIG. 5. The results show that the RT-qPCR was a valid method to analyze RNA species in an RNA mixture in terms of identity and quantity.

In the present experiment, target sequence specific primers were used in the RT-qPCR experiments. Such a setup requires a thorough and time-consuming primer design, and may not be applicable for highly similar RNA mixtures.

Example 10: RT-qPCR for the Analysis of RNA Mixtures Using Plasmid Encoded Tags

The goal of this experiment is to establish a target sequence independent RT-qPCR for the analysis of RNA mixtures. In contrast to Example 9, coding-sequence independent tags are used to quantify RNA species in an RNA mixture.

As a proof-of-principle experiment, plasmids are generated, harboring distinctive sequence regions (70-100 nucleotides) for PCR amplification. Cloning is performed as described in Example 3. The obtained expression vectors are used to generate different mRNAs via RNA in vitro transcription (according to Example 4) to obtain mRNA species harboring distinctive PCR tags in their UTR regions. The RT-qPCR is performed according to Example 9, using PCR-tag specific primers.

The invention claimed is:

1. A method of analyzing a sample comprising at least two different RNA species, each having a sequence comprising a target sequence that is a distinctive protein coding sequence and a distinctive PCR tag in a 3' untranslated region (UTR), said at least two different RNA species prepared by RNA in vitro transcription, the method comprising determining the presence, integrity and/or quantity of each of the RNA species present in said sample using RT-qPCR that comprises the following steps:

a) contacting said sample with at least one primer for reverse transcription under conditions sufficient for reverse transcription, thereby providing a sample containing cDNA;

b) contacting the sample containing cDNA with different sets of PCR primers under conditions sufficient for PCR amplification of the cDNA, wherein each set of PCR primers includes one primer capable of binding to the distinctive PCR tag of the cDNA corresponding to one RNA species within the sample, but not to the cDNA corresponding to other RNA species within the sample, thereby producing amplified DNA corresponding to the at least two different RNA species; and c) quantifying the amplified DNA corresponding to the at least two different RNA species, wherein said at least two different RNA species are at least 200 nucleotides in length and: (1) have a length that is no more than 10% different from one another; and (2) 3' UTR sequences that are at least 80% identical to one another.

2. The method according to claim 1, wherein the distinctive PCR tag is a synthetic sequence.

3. The method according to claim 1, wherein the amplified DNA is quantified using a fluorescent dye.

4. The method according to claim 3, wherein a different fluorescent dye is used for each amplified DNA corresponding to one RNA species.

5. The method according to claim 1, wherein the at least one primer for reverse transcription is complimentary to a sequence in the 3'UTR of said different RNA species.

6. The method according to claim 1, wherein the different RNA species comprise at least four three different RNA species.

7. The method according to claim 6, wherein the three different RNA species encode different influenza HA antigens.

8. The method according to claim 7, wherein the three different RNA species encode different influenza HA antigens from influenza A and influenza B.

9. The method according to claim 8, wherein the three different RNA species encode H1 and H3 antigens from influenza A and a HA antigen from influenza B.

10. The method according to claim 1, wherein said at least two different RNA species have a length that is no more than 5% different from one another.

11. The method according to claim 1, wherein said at least two different RNA species are at least 600 nucleotides in length.

12. The method of claim 1, wherein the distinctive PCR tag is 70-100 nucleotides in length.

13. The method of claim 1, wherein the at least two RNA species each comprises, from 5' to 3', a 5' Cap, the distinctive protein coding sequence, the 3' UTR, and a poly(A) sequence.

14. The method of claim 1, wherein the poly(A) is 60 to 250 adenosine nucleotides in length.

15. The method of claim 14, wherein the at least one primer for reverse transcription is an oligo (dT) primer.

16. The method of claim 14, wherein the 3' UTR of each of the at least two RNA species comprise a sequence derived from a β-globin gene.

17. The method of claim 14, wherein the 3' UTR of each of the at least two RNA species are at least 85% identical to one another.

18. The method of claim 17, wherein the 3' UTR of each of the at least two RNA species are at least 90% identical to one another.

* * * * *

SEQUENCE LISTING

<160> NUMBER OF SEQ ID NOS: 37

<210> SEQ ID NO 1
<211> LENGTH: 1701
<212> TYPE: RNA
<213> ORGANISM: artificial
<220> FEATURE:
<223> OTHER INFORMATION: GC optimized sequence encoding H3N2

<400> SEQUENCE: 1

```
augaagacca ucaucgcccu gagcuacauc cucugccugg uguucgccca gaagcugccc        60
ggcaacgaca acuccaccgc gacgcucugc cuggggcacc acgccguccc gaacggcacc       120
aucgugaaga ccaucaccaa cgaccgcauc gaggugacga acgccaccga gcugguccag       180
aacagcucca ucggggagau cugcgacagc ccccaccaga uccucgacgg cgagaacugc       240
acccugaucg acgcccugcu cggggacccc cagugcgacg gcuuccagaa caagaagugg       300
gaccuguucg uggagcgguc caaggccuac agcaacugcu accccuacga cgugccggac       360
uacgcguccc ugcgcagccu cgucgccucc agcggcaccc uggaguucaa caacgaguuc       420
uucaacugga cggggugac gcagaacggc accagcuccg ccugcauccg gcgcagcaac       480
aacuccuucu ucagccggcu gaacuggcuc acccaccuga acuucaagua ccccgcccug       540
aacgugacca ugcccaacaa cgagcaguuc gacaagcucu acaucugggg cguccaccac       600
cccgggacgg acaaggacca gaucuuccug uacgcgcagc cguccgggcg caucaccgug       660
agcaccaagc ggucccagca ggccgugauc cccaacaucg gcagccgccc cggauccgc        720 aacaucccga gccggaucuc caucuacugg accaucguca gcccggcga cauccugcuc        780 aucaacagca cggggaaccu gaucgccccg cgcggcuacu ucaagauccg guccgggaag       840
agcuccauca ugcgcagcga cgcccccauc ggcaagugca guccgagug cauccccccc        900 aacggcagca ucccgaacga caagcccuuc cagaacguga accggaucac cuacggggcc       960
ugcccccgcu acgugaagca guccacccug aagcucgcga cgggcaugcg gaacgucccc      1020
gagaagcaga cccgcgggau cuucggcgcc aucgccgggu ucaucgagaa cggcugggag      1080
ggcauggugg acgggugua cggcuuccgg caccagaaca gcgaggggcg cggccaggcc      1140
gccgaccuga aguccacccca ggcggccauc gaccagauca cgggaagcu gaaccggcuc      1200 aucggcaaga ccaacgagaa guuccaccag aucgagaagg aguucagcga gguggaggc       1260 cgcauccagg accuggagaa guacgucgag gacacgaaga ucgaccugug guccuacaac      1320
gccgagcucc uggugccu ggagaaccag cacaccaucg accucaccga cagcgagaug        1380
aacaagcugu ucgagaagac caagaagcag cugcgcgaga cgccgagga cauggggaac       1440 ggcugcuuca gaaucuacca caagugcgac aacgcgugca ucgggucca ccggaacggc        1500 acguacgacc acgacguua ccgcgacgag gccctcaaca accgguucca gaucaagggg       1560
gucgagcuga agagcggcua caaggacugg auccugugga ucuccuucgc caucagcugc      1620
uuccuccugu gcguggcccu gcucggcuuc aucaugugg ccugccagaa ggggaacauc        1680
cgcugcaaca ucugcaucug a                                              1701
```

<210> SEQ ID NO 2
<211> LENGTH: 1701
<212> TYPE: RNA
<213> ORGANISM: artificial
<220> FEATURE:
<223> OTHER INFORMATION: GC optimized sequence encoding H1N1

<400> SEQUENCE: 2

-continued

```
augaaggcca uccugguggu ccuccuguac accuucgcca ccgcgaacgc cgacacgcug    60
ugcaucggcu accacgccaa caacagcacc gacaccgugg acaccgugcu cgagaagaac   120
gucacgguga cccacuccgu gaaccugcug gaggacaagc acaacgggaa gcucugcaag   180
cugcggggcg ucgccccgcu gcaccucggg aagugcaaca ucgccggcug gauccugggg   240
aacccggagu gcgagagccu guccaccgcg agcuccugga gcuacaucgu ggagaccccc   300
uccagcgaca acggcacgug cuaccccggc gacuucaucg acuacgagga gcuccgcgag   360
cagcugucca gcguguccag cuucgagcgg uucgagaucu uccccaagac cuccagcugg   420
ccgaaccacg acuccgacaa gggggucacc gccgccugcc cccacgccgg cgcgaagagc   480
uucuacaaga accugaucug gcucgugaag aaggggaacu ccuaccccaa gcugagcaag   540
uccuacauca cgacaagggg caaggaggug cugguccucu gggggauucca ccaccccagc   600 accagcgccg accagcaguc ccuguaccag aacgccgacg ccuacguguu cguggggcagc   660 ucccgcuaca gcaagacguu caagccggag aucgccaucc ggcccaaggu ccgcgaccgg   720
gagggccgca ugaacuacua cuggacccug guggagcccg gggacaagau caccuucgag   780
gcgaccggca accucguggu cccccgguac gccuucgcca uggagcgcaa cgccgggucc   840
ggcaucauca ucagcgacac gccggugcac gacugcaaca ccaccugcca gaccccccaag   900 ggcgccauca acacgucccu gcccuuccag aacauccacc ccaucaccau cgggaagugc   960
ccgaaguacg ugaagagcac caagcugcgg cucgcgaccg gccugcgcaa caucccccucc   1020 auccagagcc gggggcuguu cggcgccauc gccgggguuca ucgagggcgg cuggacgggg   1080 augggucgacg gcugguacgg guaccaccac cagaacgagc agggcagcgg guacgccgcc   1140
gaccucaagu ccacgcagaa cgcgaucgac gagaucacca caaaggugaa cagcgucauc   1200
gagaagauga acacccaguu caccgccgug ggcaaggagu ucaaccaccu ggagaagcgg   1260
aucgagaacc ugaacaagaa ggucgacgac ggcuuccucg acaucuggac guacaacgcc   1320
gagcugcugg ugcuccugga gaacgagcgc acccuggacu accacgacuc caacgugaag   1380
aaccucuacg agaagguccg gagccagcug aagaacaacg ccaaggagau cgggaacggc   1440
ugcuucgagu ucuaccacaa gugcgacaac accugcaugg aguccgugaa gaacgggacc   1500
uacgacuacc ccaaguacag cgaggaggcc aagcugaacc gcgaggagau cgacggcgug   1560
aagcucgagu ccacgcggau cuaccagauc cuggcgaucu acagcaccgu cgccagcucc   1620
cuggugcucg uggucagccu gggggccauc uccuucugga ugugcagcaa cggcucccug   1680
cagugccgca ucugcaucug a                                            1701
```

<210> SEQ ID NO 3
<211> LENGTH: 1755
<212> TYPE: RNA
<213> ORGANISM: artificial
<220> FEATURE:
<223> OTHER INFORMATION: GC optimized sequence encoding HA influenza B

<400> SEQUENCE: 3

```
augaaggcca ucaucgugcu gcucaugguc gugaccagca cgccgaccg caucugcacc     60 ggcaucacgu ccagcaacuc cccgcacgug gucaagaccg cgacccaggg ggaggugaac    120
gugaccggcg ucaucccccu gacgaccacc cccaccaaga gcuacuucgc caaccugaag    180
gggacgaaga cccggggcaa gcucugcccc gacugccuga acugcaccga ccuggacgug    240
gcccucgggc gccccaugug cguggggcacc acgccguccg ccaaggccag cauccugcac    300
```

-continued

```
gagguccggc ccgugaccuc cggcugcuuc cccaucaugc acgaccgcac caagauccgg      360
cagcuggcga accuccugcg cggguacgag aacauccggc ugagcaccca gaacgugauc      420
gacgccgaga aggcccccgg cgggccguac cgccucggca cguccgggag cugccccaac      480
gccaccucca agagcggcuu cuucgcgacc auggccuggg ccguccccaa ggacaacaac      540
aagaacgcca ccaacccccu gacgguggag gugccguaca ucugcgccga gggcgaggac      600
cagaucaccg ucuggggguu ccacuccgac gacaagaccc agaugaagaa ccuguacggc      660
gacagcaacc cccagaaguu caccuccagc gcgaacgggg ugacgaccca cuacgugucc      720
cagaucggcg gcuuccccga ccagaccgag gacggggggcc uccccagag cgggcggauc       780 gucguggacu acaugaugca gaagccgggc aagaccggga cgaucgugua ccagcgcggc      840
guccugcugc cccagaaggu guggugcgcc uccggccgga gcaaggugau caaggggagc      900
cucccccuga ucggcgaggc cgacugccug cacgagaagu acggggggccu caacaagucc      960 aagccguacu acaccgggga gcacgccaag gccaucggca acugcccau cugggucaag      1020 accccgcuga agcuggcgaa cggcaccaag uaccgcccgc ccgccaagcu ccugaaggag      1080 cgggggguucu ucggcgccau cgccgggguuc cuggaggggcg gguggagggg caugaucgcc      1140
ggcuggcacg gguacacgag ccacggcgcg cacggggugg ccgucgccgc cgaccucaag      1200
uccacccagg aggccaucaa caagaucacc aagaaccuga acagccuguc cgagcucgag      1260
gugaagaacc ugcagcgccu gagcggcgcg auggacgagc uccacaacga gauccuggag      1320
cuggacgaga aggguggacga ccuccgggcc gacaccaucu ccagccagau cgagcuggcc      1380
guccugcucu ccaacgaggg caucaucaac agcgaggacg agcaccugcu ggcccucgag      1440
cgcaagcuga agaagaugcu gggggccgucc gcggguggaca ucggcaacgg gugcuucgag      1500
acgaagcaca agugcaacca gaccugccuc gaccggaucg ccgccggcac cuucaacgcc      1560 ggggagguuca gccugcccac cuucgacucc cugaacauca ccgccgcgag ccugaacgac      1620
gacggccucg acaaccacac gauccugcug uacuaucca ccgccgccag cucccucgcc       1680
gugacccuga ugcuggccau cuucaucguc uacaugguga ccgcgacaa cgugucecugc      1740 agcaucugcc ucuga                                                       1755
```

<210> SEQ ID NO 4
<211> LENGTH: 1758
<212> TYPE: RNA
<213> ORGANISM: artificial
<220> FEATURE:
<223> OTHER INFORMATION: GC optimized sequence encoding HA influenza B
      Brisbane

<400> SEQUENCE: 4

```
augaaggcca ucaucgugcu gcucaugguc ugugaccagc acgccgaccg gaucugcacc      60
ggcaucacgu ccagcaacuc cccgcacgug gucaagaccg cgacccaggg ggagggugaac       120 gugaccggcg ucaucccgcu gacgaccacc cccaccaaga gccacuucgc caaccugaag      180
gggacggaga cccgcggcaa gcucugcccc aagugccuga acugcaccga ccuggacgug      240
gcccucgggc ggcccaagug caccggcaag auccgguccg cccgcgugag cauccugcac      300 gaggucggc ccgugacguc cggcugcuuc cccaucaugc acgaccgcac caagauccgg       360
cagcugccca accuccugcg cggguacgag cacauccggc ugagcaccca caacgugauc      420
aacgccgaga acgcgccggg cgggcccuac aagauccggca ccuccgggag cugccccaac      480
aucacgaacg gcaacggcuu cuucgccacc auggccuggg ccgucecccaa gaacgacaag      540
```

-continued

```
aacaagaccg cgaccaaccc gcucacgauc gaggugcccu acaucugcac cgaggggggag        600 gaccagauca ccgugugggg cuuccacucc gacaacgaga cccagauggc caagcuguac        660
ggggacagca agcccagaa guucacgucc agcgccaacg gcgucaccac ccacuacgug         720
ucccagaucg gcggguuccc caaccagacc gaggacggcg ggctgccgca gagcggccgc        780
aucguggucg acuacauggu gcagaagucc gggaagacgg gcaccaucac cuaccagcgg        840
ggcauccucc ugccccagaa ggugguggug ccagcgggc gcuccaaggu caucaagggc        900
agccugcccc ucaucgggga ggccgacugc cugcacgaga aguacggcgg gcugaacaag        960
agcaagcccu acuacaccgg cgagcacgcg aaggccaucg gcaacugccc gaucuggggug     1020 aagacgcccc ucaagcuggc caacgggacc aaguaccggc ccccgccaa gcugcucaag       1080 gagcgcggcu ucuucggggc caucgcgggc uuccuggagg cggguuggga gggcaugauc      1140 gccgggugc acggcuacac cucccacggg gcccacggcg uggccgucgc cgcggaccug       1200
aagagcaccc aggaggccau caacaagauc acgaagaacc ucaacuccu gagcgagcug      1260 gaggugaaga accuccagcg gcugucggc gccauggacg agcugcacaa cgagauccuc       1320
gagcuggacg agaaggucga cgaccugcgc gccgacacca ucagcuccca gaucgagcuc      1380
gccgugcugc ugagcaacga ggggaucauc aacuccgagg acgagcaccu ccuggcgcug      1440
gagcggaagc ucaagaagau gcugggcccg agcgccgugg agaucgggaa cggcugcuuc      1500
gagaccaagc acaagugcaa ccagaccugc cuggaccgca ucgccgccgg gaccuucgac      1560
gcgggcgagu ucucccucccc cacguucgac agccugaaca ucaccgccgc cucccugaac     1620
gacgacggcc uggacaacca caccauccuc cguuacuaca gcaccgccgc cuccagccug     1680
gcggucacgc ucaugaucgc caucuucgug guguacaugg ucucccggga caacgugagc     1740
ugcuccaucu gccuguga                                                    1758
```

<210> SEQ ID NO 5
<211> LENGTH: 31
<212> TYPE: DNA
<213> ORGANISM: artificial
<220> FEATURE:
<223> OTHER INFORMATION: molecular beacon CU

<400> SEQUENCE: 5

```
cgaggtgttg aagagaagtt gcttgtcctc g                                       31
```

<210> SEQ ID NO 6
<211> LENGTH: 31
<212> TYPE: DNA
<213> ORGANISM: artificial
<220> FEATURE:
<223> OTHER INFORMATION: molecular beacon FR

<400> SEQUENCE: 6

```
cgaggttccg agctaactgt atttctcctc g                                       31
```

<210> SEQ ID NO 7
<211> LENGTH: 31
<212> TYPE: DNA
<213> ORGANISM: artificial
<220> FEATURE:
<223> OTHER INFORMATION: molecular beacon NU

<400> SEQUENCE: 7

```
cgaggaactg atgtcttgaa attaaccctc g                                       31
```

-continued

```
<210> SEQ ID NO 8
<211> LENGTH: 31
<212> TYPE: DNA
<213> ORGANISM: artificial
<220> FEATURE:
<223> OTHER INFORMATION: molecular beacon SP

<400> SEQUENCE: 8
cgaggtctcc tattaatgct tgtcaccctc g                                    31

<210> SEQ ID NO 9
<211> LENGTH: 73
<212> TYPE: DNA
<213> ORGANISM: artificial
<220> FEATURE:
<223> OTHER INFORMATION: 3' part of the 3' UTR

<400> SEQUENCE: 9
aaaaaaaatg catcccccc cccccccccc cccccccccc ccccaaaggc tcttttcaga    60
gccaccagaa ttc                                                        73

<210> SEQ ID NO 10
<211> LENGTH: 64
<212> TYPE: DNA
<213> ORGANISM: artificial
<220> FEATURE:
<223> OTHER INFORMATION: primer CU forward

<400> SEQUENCE: 10
gtcctcatgc atcccccccc cccccccccc cccccccccc cccacaagca acttctcttc    60
aaca                                                                  64

<210> SEQ ID NO 11
<211> LENGTH: 56
<212> TYPE: DNA
<213> ORGANISM: artificial
<220> FEATURE:
<223> OTHER INFORMATION: primer CU reverse

<400> SEQUENCE: 11
catggtgaat tctggtggct ctgaaaagag ccttttgttg aagagaagtt gcttgt        56

<210> SEQ ID NO 12
<211> LENGTH: 64
<212> TYPE: DNA
<213> ORGANISM: artificial
<220> FEATURE:
<223> OTHER INFORMATION: primer FR forward

<400> SEQUENCE: 12
gtcctcatgc atcccccccc cccccccccc cccccccccc cccagaaata cagttagctc    60
ggaa                                                                  64

<210> SEQ ID NO 13
<211> LENGTH: 56
<212> TYPE: DNA
<213> ORGANISM: artificial
<220> FEATURE:
<223> OTHER INFORMATION: primer FR reverse

<400> SEQUENCE: 13
catggtgaat tctggtggct ctgaaaagag cctttttccg agctaactgt atttct        56

<210> SEQ ID NO 14
```

-continued

```
<211> LENGTH: 64
<212> TYPE: DNA
<213> ORGANISM: artificial
<220> FEATURE:
<223> OTHER INFORMATION: primer NU forward

<400> SEQUENCE: 14
gtcctcatgc atcccccccc cccccccccc cccccccccc cccgttaatt tcaagacatc      60
agtt                                                                    64

<210> SEQ ID NO 15
<211> LENGTH: 56
<212> TYPE: DNA
<213> ORGANISM: artificial
<220> FEATURE:
<223> OTHER INFORMATION: primer NU reverse

<400> SEQUENCE: 15
catggtgaat tctggtggct ctgaaaagag cctttaactg atgtcttgaa attaac         56

<210> SEQ ID NO 16
<211> LENGTH: 64
<212> TYPE: DNA
<213> ORGANISM: artificial
<220> FEATURE:
<223> OTHER INFORMATION: primer SP forward

<400> SEQUENCE: 16
gtcctcatgc atcccccccc cccccccccc cccccccccc cccgtgacaa gcattaatag      60
gaga                                                                    64

<210> SEQ ID NO 17
<211> LENGTH: 56
<212> TYPE: DNA
<213> ORGANISM: artificial
<220> FEATURE:
<223> OTHER INFORMATION: primer SP reverse

<400> SEQUENCE: 17
catggtgaat tctggtggct ctgaaaagag ccttttctcc tattaatgct tgtcac         56

<210> SEQ ID NO 18
<211> LENGTH: 21
<212> TYPE: RNA
<213> ORGANISM: artificial
<220> FEATURE:
<223> OTHER INFORMATION: CU target oligonucleotide

<400> SEQUENCE: 18
acaagcaacu ucucuucaac a                                                 21

<210> SEQ ID NO 19
<211> LENGTH: 21
<212> TYPE: RNA
<213> ORGANISM: artificial
<220> FEATURE:
<223> OTHER INFORMATION: FR target oligonucleotide

<400> SEQUENCE: 19
agaaauacag uuagcucgga a                                                 21

<210> SEQ ID NO 20
<211> LENGTH: 21
<212> TYPE: RNA
<213> ORGANISM: artificial
```

<220> FEATURE:
<223> OTHER INFORMATION: NU target oligonucleotide

<400> SEQUENCE: 20
guuaauuuca agacaucagu u                                        21

<210> SEQ ID NO 21
<211> LENGTH: 21
<212> TYPE: RNA
<213> ORGANISM: artificial
<220> FEATURE:
<223> OTHER INFORMATION: SP target oligonucleotide

<400> SEQUENCE: 21
gugacaagca uuaauaggag a                                        21

<210> SEQ ID NO 22
<211> LENGTH: 27
<212> TYPE: DNA
<213> ORGANISM: artificial
<220> FEATURE:
<223> OTHER INFORMATION: DNA probe S1

<400> SEQUENCE: 22
gtcccacttc ttgttctgga agccgtc                                  27

<210> SEQ ID NO 23
<211> LENGTH: 27
<212> TYPE: DNA
<213> ORGANISM: artificial
<220> FEATURE:
<223> OTHER INFORMATION: DNA probe S4

<400> SEQUENCE: 23
ccaggagctc gcggtggaca ggctctc                                  27

<210> SEQ ID NO 24
<211> LENGTH: 22
<212> TYPE: DNA
<213> ORGANISM: artificial
<220> FEATURE:
<223> OTHER INFORMATION: DNA probe S8

<400> SEQUENCE: 24
atggtcgcga agaagccgct ct                                       22

<210> SEQ ID NO 25
<211> LENGTH: 27
<212> TYPE: DNA
<213> ORGANISM: artificial
<220> FEATURE:
<223> OTHER INFORMATION: DNA probe S10

<400> SEQUENCE: 25
cacgcgggcg gacgggatct tgccggt                                  27

<210> SEQ ID NO 26
<211> LENGTH: 21
<212> TYPE: DNA
<213> ORGANISM: artificial
<220> FEATURE:
<223> OTHER INFORMATION: probe S1_CU

<400> SEQUENCE: 26
tgttgaagag aagttgcttg t                                        21

-continued

```
<210> SEQ ID NO 27
<211> LENGTH: 21
<212> TYPE: DNA
<213> ORGANISM: artificial
<220> FEATURE:
<223> OTHER INFORMATION: probe S1_FR

<400> SEQUENCE: 27
ttccgagcta actgtatttc t                                               21

<210> SEQ ID NO 28
<211> LENGTH: 21
<212> TYPE: DNA
<213> ORGANISM: artificial
<220> FEATURE:
<223> OTHER INFORMATION: probe S1_NU

<400> SEQUENCE: 28
aactgatgtc ttgaaattaa c                                               21

<210> SEQ ID NO 29
<211> LENGTH: 21
<212> TYPE: DNA
<213> ORGANISM: artificial
<220> FEATURE:
<223> OTHER INFORMATION: probe S1_SP

<400> SEQUENCE: 29
tctcctatta atgcttgtca c                                               21

<210> SEQ ID NO 30
<211> LENGTH: 20
<212> TYPE: DNA
<213> ORGANISM: artificial
<220> FEATURE:
<223> OTHER INFORMATION: H3N2 forward primer

<400> SEQUENCE: 30
cccatcggca agtgcaagtc                                                 20

<210> SEQ ID NO 31
<211> LENGTH: 20
<212> TYPE: DNA
<213> ORGANISM: artificial
<220> FEATURE:
<223> OTHER INFORMATION: H3N2 reverse primer

<400> SEQUENCE: 31
ccggttcacg ttctggaagg                                                 20

<210> SEQ ID NO 32
<211> LENGTH: 20
<212> TYPE: DNA
<213> ORGANISM: artificial
<220> FEATURE:
<223> OTHER INFORMATION: H1N1 forward primer

<400> SEQUENCE: 32
ggagaagcgg atcgagaacc                                                 20

<210> SEQ ID NO 33
<211> LENGTH: 20
<212> TYPE: DNA
<213> ORGANISM: artificial
<220> FEATURE:
<223> OTHER INFORMATION: H1N1 reverse primer
```

-continued

```
<400> SEQUENCE: 33
cggcgttgta cgtccagatg                                                  20

<210> SEQ ID NO 34
<211> LENGTH: 17
<212> TYPE: DNA
<213> ORGANISM: artificial
<220> FEATURE:
<223> OTHER INFORMATION: influenza B massachusetts forward primer

<400> SEQUENCE: 34
ccaaccccct gacggtg                                                     17

<210> SEQ ID NO 35
<211> LENGTH: 20
<212> TYPE: DNA
<213> ORGANISM: artificial
<220> FEATURE:
<223> OTHER INFORMATION: influenza B Massachusetts reverse primer

<400> SEQUENCE: 35
tgtcgccgta caggttcttc                                                  20

<210> SEQ ID NO 36
<211> LENGTH: 21
<212> TYPE: DNA
<213> ORGANISM: artificial
<220> FEATURE:
<223> OTHER INFORMATION: influenza B Brisbane forward primer

<400> SEQUENCE: 36
cacccacaac gtgatcaacg c                                                21

<210> SEQ ID NO 37
<211> LENGTH: 20
<212> TYPE: DNA
<213> ORGANISM: artificial
<220> FEATURE:
<223> OTHER INFORMATION: influenza B Brisbane reverse primer

<400> SEQUENCE: 37
gttgccgttc gtgatgttgg                                                  20
```